United States Patent [19]
Kiefer et al.

[11] Patent Number: 6,015,687
[45] Date of Patent: Jan. 18, 2000

[54] APOPTOSIS-MODULATING PROTEINS, DNA ENCODING THE PROTEINS AND METHODS OF USE THEREOF

[75] Inventors: Michael C. Kiefer, Clayton; Philip J. Barr, Berkeley, both of Calif.

[73] Assignee: LXR Biotechnology Inc., Richmond, Calif.

[21] Appl. No.: 08/471,057

[22] Filed: Jun. 6, 1995

Related U.S. Application Data

[60] Division of application No. 08/320,157, Oct. 7, 1994, which is a continuation-in-part of application No. 08/160,067, Nov. 30, 1993, abandoned.

[51] Int. Cl.⁷ .......................... C12N 15/00; C12N 15/09; C12N 15/63
[52] U.S. Cl. ..................... 435/69.1; 435/325; 435/320.1; 435/91.2; 435/455
[58] Field of Search .......................... 514/44; 435/172.3, 435/69.1, 325, 91.2, 320.1, 455; 424/93.21; 935/23, 78, 79, 70, 71; 536/23.1, 23.5, 24.31

[56] References Cited

FOREIGN PATENT DOCUMENTS

| | | |
|---|---|---|
| WO 93/04169 | 3/1993 | WIPO . |
| WO 94/00572 | 1/1994 | WIPO . |
| WO 95/00160 | 1/1995 | WIPO . |
| WO 95/00642 | 1/1995 | WIPO . |
| WO 95/05738 | 3/1995 | WIPO . |
| WO 95/05750 | 3/1995 | WIPO . |
| WO 95/15084 | 6/1995 | WIPO . |
| WO96/05232 | 2/1996 | WIPO . |
| WO 96/33416 | 10/1996 | WIPO . |
| WO 96/35951 | 11/1996 | WIPO . |

OTHER PUBLICATIONS

Hickish et al., "Ultrastructural localization of BHRF1: An Epstein–Barr virus gene product which has homology with bcl–2" *Cancer Research* (1994) 54:2808–2811.

Tarodi et al., "Epstein–Barr virus BHRF1 protein protects against cell death induced by DNA–damaging agents and heterologous viral infection" *Virology* (1994) 201:404–407.

Dialog® Abstract of PCT WO 96/05232 (Feb. 22, 1996). One page total.

Dialog® Abstract of PCT WO 96/35951 (Nov. 14, 1996). One page total.

Lewin , "When does homology mean something else?" *Science* (1987) 237:1570.

Reeck et al., "'Homology' in proteins and nucleic acids: a terminology muddle and a way out of it" *Cell* (1987) 50:667.

Dzau et al., "Fusigenic viral liposome for gene therapy in cardiovascular diseases" *Proc. Natl. Acad. Sci. USA* (1996) 93:11421–11425.

Dorin et al., "A demonstration using mouse models that successful gene therapy for cystic fibrosis requires only partial gene correction" *Gene Ther.* (1996) 3:797–801.

Buckel, "Recombinant proteins for therapy" *Trends Pharm. Sci.* (1996) 17:450–456.

Norrby, "Angiogenesis: New aspects relating to its initiation and control" *APMIS* (1997) 105:417–437.

Grossman et al., "A small step for gene therapy" *Nat. Genet.* (1994) 6:323–324.

Klein, "Cellular gene therapy: An overview" *J. Clin. Apheresis* (1994) 9:139–141.

Keating et al., "Gene transfer by electroportation: A model for gene therapy" *Bone Marrow Purging and Processing*(1990) 333:491–498.

Chittenden et al., "Induction of apoptosis by the Bcl–2 homologue Bak" *Nature* (1995) 347:733–736.

Farrow et al., "Cloning of a bcl–2 homologue by interaction with adenovirus E1B 19K" *Nature* (1995) 374:731–733.

Kiefer et al., "Modulation of apoptosis by the widely distributed Bcl–2 homologue Bak" *Nature* (1995) 374:736–739.

Nuñez et al., "Deregulated Bcl–2 gene expression selectively prolongs survival of growth factor–deprived homopoietic cell lines" *J. Immunol.* (1990) 144:3602–3610.

Hockenbery et al., "Bcl–2 is an inner mitochondrial protein that blocks programmed cell death" *Nature* (1990) 348:334–336.

Cherif et al., "Ordering markers in the region of the ataxia–telangiectasia gene (11q22–q23) by fluorescence in situ hybridization (FISH) to interphase nuclei" *Hum. Genet.* (1994) 93:1–6.

Foroud et al., "Localization of an ataxia–telangiectasia locus to a 3–cM interval on chromosme 11q23: Linkage analysis of III families by an international consortium" *Am. J. Hum. Genet.* (1991) 49:1263–1279.

Kapp et al., "Cloning of a candidate gene for ataxia–telangiectasia group D" *Am. J. Hum. Genet.* (1992) 51:45–54.

Khati et al., "Genetic heterogeneity of autosomal dominant cerebellar ataxia type 1: Clinical and genetic analysis of 10 French families" *Neurology* (1993) 43:1131–1137.

Meyn, "Ataxia–telangiectasia, apoptosis and cellular responses to DNA damage: A model" *Cancer Genet.* (1993) 53:(Abstract No. 1529).

Orr et al., "Expansion of an unstable trinucleotide CAG repeat in spinocerebellar ataxia type 1" *Nature Genetics* (1993) 4:221–226.

Kennedy, "Prevention of carcinogenesis by protease inhibitors" *Cancer Res.* (1994) 54:1999s–2005s.

Lam et al., "Evidence that BCL–2 represses apoptosis by regulating endoplasmic reticulum–associated $Ca^{2+}$ fluxes" *Proc. Natl. Acad. Sci. USA* (1994) 91:6569–6573.

Reed et al., "Antisense–mediated inhibition of BCL2 protooncogene expression and leukemic cell growth and survival: Comparisons of phosphodiester and phosphorothioate oligodeoxynucleotides" *Cancer Res.* (1990) 50:6565–6570.

(List continued on next page.)

*Primary Examiner*—Brian R. Stanton
*Assistant Examiner*—Jill D. Martin
*Attorney, Agent, or Firm*—Morrison & Foerster

[57] ABSTRACT

The present invention provides a novel family of apoptosis–modulating proteins. Nucleotide and amino acid residue sequences and methods of use thereof are also provided.

1 Claim, 25 Drawing Sheets-

OTHER PUBLICATIONS

Yonehara et al., "A cell–killing monoclonal antibody (Anti–Fas) to a cell surface antigen co–downregulated with the receptor of tumor necrosis factor" *J. Exp. Med.* (1989) 169:1747–1756.

Wyllie, "Glucocorticoid–induced thymocyte apoptosis is associated with endogenous endonuclease activation" *Nature* (1980) 284:555–556.

Kanter et al., "Epidermal growth factor and tumor promoters prevent DNA fragmentation by different mechanisms" *Biochem. Biophys. Res. Commun.* (1984) 118:392–399.

Duke et al., "IL–2 addiction: Withdrawal of growth factor activates a suicide program in dependent T cells" *Lymphokine Res.* (1986) 5:289–299.

Tomei et al., "Inhibition of radiation–induced apoptosis in vitro by tumor promoters" *Biochem. Biophys. Res. Commun.* (1988) 155:324–331.

Kruman et al., "Apoptosis of murine BW 5147 thymoma cells induced by dexamethasone and γ–irradiation" *J. Cell Physiol.* (1991) 148:267–273.

Ameisen et al., "Cell dysfunction and depletion in AIDS: The programmed cell death hypothesis" *Immunol. Today* (1991) 12:102–105.

Sheppard et al., "The relationship between AIDS and immunologic intolerance" *J. AIDS* (1992) 5:143–147.

Gerschenson et al., "Apoptosis: A different type of cell death" *FASEB J.* (1992) 6:2450–2455.

Cohen et al., "Apoptosis and programmed cell death in immunity" *Ann. Rev. Immunol.* (1992) 10:267–293.

Tsujimoto et al., "Cloning of the chromosome breakpoint of neoplastic B cells with the t(14;18) chromosome translocation" *Science* (1984) 226:1097–1099.

Cleary et al., "Cloning and structural analysis of cDNAs for bcl–2 and a hybrid bcl–2/immunoglobin transcript resulting from the t(14;18) translocation" *Cell* (1986) 47:19–28.

McDonnell et al., "Progression from lymphoid hyperplasia to high–grade malignant lymphoma in mice transgenic for the t(14;18)" *Nature* (1991) 349:254–256.

Edgington, "Looking death in the eye: Apoptosis and cancer research" *Biotechnol.* (1993) 11:787–792.

Sentman et al., "bcl–2 inhibits multiple forms of apoptosis but not negative selection in thymocytes" *Cell* (1991) 67:879–888.

Strasser, "bcl–2 transgene inhibits T cell death and perturbs thymic self–censorship" *Cell* (1991) 67:889–899.

Hockenbery et al., "Bcl–2 functions in an antioxidant pathway to prevent apoptosis" *Cell* (1993) 75:241–251.

Williams et al., "Molecular regulation of apoptosis: genetic controls on cell death" *Cell* (1993) 74:777–779.

Zhu et al., "Systemic gene expression after intravenous DNA delivery into adult mice" *Science* (1993) 261:209–211.

Veis et al., "Bcl–2–deficient mice demonstrate fulminant lymphoid apoptosis, polycystic kidneys, and hypopigmented hair" *Cell* (1993) 75:229–240.

Kiefer et al., "Molecular cloning of a new human insulin–like growth factor binding protein" *Biochem. Biophys. Res. Commun.* (1991) 176:219–225.

Sanger et al., "DNA sequencing with chain–terminating inhibitors" *Proc. Natl. Acad. Sci. USA* (1977) 74:5463–5467.

Boise et al., "bcl–x, a bcl–2–related gene that functions as a dominant regulator of apoptotic cell death" *Cell* (1993) 74:597–608.

Oltvai et al., "Bcl–2 heterodimerizes in vivo with a conserved homolog, Bax, that accelerates programed cell death" *Cell* (1993) 74:609–619.

Zapf et al., "Isolation from adult human serum of four insulin–like growth factor (IGF) binding proteins and molecular cloning of one of them that is increased by IGF I administration and in extrapancreatic tumor hypoglycemia" *J. Biol. Chem.* (1990). 265:14892–14898.

Feinberg et al., "A technique for radiolabeling DNA restriction endonuclease fragments to high specific activity" *Anal. Biochem.* (1984) 137:266–267.

Chen–Levy et al., "The bcl–2 candidate proto–oncogene product is a 24–kilodalton integral–membrane protein highly expressed in lymphoid cell lines and lymphomas carrying the t(14;18) translocation" *Mol. Cell. Biol.* (1989) 9:701–710.

Jacobson et al., "Bcl–2 blocks apoptosis in cells lacking mitochondrial DNA" *Nature* (1993) 361:365–369.

Monaghan et al., "Ultrastructural localization of BCL–2 protein" *J. Histochem. Cytochem.* (1992) 40:1819–1825.

Lehrach et al., "RNA molecular weight determinations by gel electrophoresis under denaturing conditions, a critical reexamination" *Biochem.* (1977) 16:4743–4751.

Thomas, "Hybridization of denatured RNA and small DNA fragments transferred to nitrocellulose" *Proc. Natl. Acad. Sci. USA* (1980) 77:5201–5205.

Barr, "Expression of foreign genes in yeast" *Transgenesis* (1992) Murray, J.A.H., ed., Wiley & Sons, New York, pp. 55–79.

Henderson et al., "Epstein–Barr virus–coded BHRF1 protein, a viral homologue of Bcl–2, protects human B cells from programmed cell death" *Proc. Natl. Acad. Sci. USA* (1993) 90:8479–8483.

Viegas–Péquignot, "In situ hybridization to chromosomes with biotinylated probes" *In Situ Hybridization. A Practical Approach,* D.G. Wilkinson, ed., IRL Press, Oxford, pp. 137–158.

Pinkel et al., "Fluorescence in situ hybrization with human chromosome–specific libraries: Detection of trisomy 21 and translocations of chromosome 4" *Proc. Natl. Acad. Sci. USA* (1988) 85:9138–9142.

McKearn et al., "Enrichment of hematopoietic precursor cells and cloning of multipotential B–lymphocyte precursors" *Proc. Natl. Acad. Sci. USA* (1985) 82:7414–7418.

Orkin et al., Report and Recommendations of the Panel to Assess the NIH Investment in Research on Gene Therapy, Dec. 7, 1995.

Coghlan, Focus, vol. 148, pp. 14–15, Nov. 25, 1995.

Brown, "News Media, Researchers 'Oversold' Gene Therapy, Advisory Panel Says", The Washington Post, Dec. 8, 1995.

Marshall, Science, vol. 269, pp. 1050–1055, Aug. 25, 1995.

Figure 1 bcl Consensus PCR Primers

```
                              Ile
EcoRI AspTrpGlyArgValValAla
5- AGATCTGAATTCAACTTGGGGGIC(A)GIA(G)TXGTXGC -3'  bclx 1-32

AspTrpGlyGlyGlnGluAsnAspGlnIleTrp
          AGGGTIGGIGGXACXAGA(G)ACA(T)(C)TAGGT
5'- AGATCT'AAGCTTGTCCCAICCICCXTGXCC(T)TGA(G)ATCCA -3'  bclX 2-39
```

Fig. 3A

```
                10                    20                    30
                *                     *                     *
GAG GAT CTA CAG GGG ACA AGT AAA GGC TAC ATC CAG
CTC CTA GAT GTC CCC TGT TCA TTT CCG ATG TAG GTC

>Aha2
        40           50         |  60                    70
        *            *             *                     *
ATG CCG GGA ATG CAC TGA CGC CCA TTC CTG GAA ACT
TAC GGC CCT TAC GTG ACT GCG GGT AAG GAC CTT TGA 80                    90                   100
         *                     *                     *
GGG CTC CCA CTC AGC CCC TGG GAG CAG CAG CCG CCA
CCC GAG GGT GAG TCG GGG ACC CTC GTC GTC GGC GGT 110                   120                   130                   140
   *                     *                     *                     *
GCC CCT CGG ACC TCC ATC TCC ACC CTG CTG AGC CAC
CGG GGA GCC TGG AGG TAG AGG TGG GAC GAC TCG GTG

>SmaI         >BamH1
 |            |
 |    150     |   160                  170                   180
 |     *      |    *                    *                     *
CCG GGT TGG GCC AGG ATC CCG GCA GGC TGA TCC CGT
GGC CCA ACC CGG TCC TAG GGC CGT CCG ACT AGG GCA 190                   200                   210
               *                     *                     *
CCT CCA CTG AGA CCT GAA AA ATG GCT TCG GGG CAA GGC
GGA GGT GAC TCT GGA CTT TT TAC CGA AGC CCC GTT CCG
                            M   A   S   G   Q   G 220                   230                   240                   250
   *                     *                     *                     *
CCA GGT CCT CCC AGG CAG GAG TGC GGA GAG CCT GCC
GGT CCA GGA GGG TCC GTC CTC ACG CCT CTC GGA CGG
 P   G   P   P   R   Q   E   C   G   E   P   A
```

Fig. 3B

```
         260                 270                 280                 290
          *                   *                   *                   *
CTG  CCC  TCT  GCT  TCT  GAG  GAG  CAG  GTA  GCC  CAG  GAC
GAC  GGG  AGA  CGA  AGA  CTC  CTC  GTC  CAT  CGG  GTC  CTG
 L    P    S    A    S    E    E    Q    V    A    Q    D 300                 310                 320
                      *                   *                   *
ACA  GAG  GAG  GTT  TTC  CGC  AGC  TAC  GTT  TTT  TAC  CGC
TGT  CTC  CTC  CAA  AAG  GCG  TCG  ATG  CAA  AAA  ATG  GCG
 T    E    E    V    F    R    S    Y    V    F    Y    R 330                 340                 350                 360
          *                   *                   *                   *
CAT  CAG  CAG  GAA  CAG  GAG  GCT  GAA  GGG  GTG  GCT  GCC
GTA  GTC  GTC  CTT  GTC  CTC  CGA  CTT  CCC  CAC  CGA  CGG
 H    Q    Q    E    Q    E    A    E    G    V    A    A 370                 380                 390
                      *                   *                   *
CCT  GCC  GAC  CCA  GAG  ATG  GTC  ACC  TTA  CCT  CTG  CAA
GGA  CGG  CTG  GGT  CTC  TAC  CAG  TGG  AAT  GGA  GAC  GTT
 P    A    D    P    E    M    V    T    L    P    L    Q

>NcoI
                    |
         400        |        410                 420                 430
          *         |         *                   *                   *
                    |
CCT  AGC  AGC  ACC  ATG  GGG  CAG  GTG  GGA  CGG  CAG  CTC
GGA  TCG  TCG  TGG  TAC  CCC  GTC  CAC  CCT  GCC  GTC  GAG
 P    S    S    T    M    G    Q    V    G    R    Q    L 440                 450                 460                 470
          *                   *                   *                   *
GCC  ATC  ATC  GGG  GAC  GAC  ATC  AAC  CGA  CGC  TAT  GAC
CGG  TAG  TAG  CCC  CTG  CTG  TAG  TTG  GCT  GCG  ATA  CTG
 A    I    I    G    D    D    I    N    R    R    Y    D
```

Fig. 3C

```
                                                    >PstI
         480              490              500       |
          *                *                *
TCA GAG TTC CAG ACC ATG TTG CAG CAC CTG CAG CCC
AGT CTC AAG GTC TGG TAC AAC GTC GTG GAC GTC GGG
 S   E   F   Q   T   M   L   Q   H   L   Q   P 510              520              530              540
      *                *                *                *
ACG GCA GAG AAT GCC TAT GAG TAC TTC ACC AAG ATT
TGC CGT CTC TTA CGG ATA CTC ATG AAG TGG TTC TAA
 T   A   E   N   A   Y   E   Y   F   T   K   I 550              560              570
          *                *                *
GCC ACC AGC CTG TTT GAG AGT GGC ATC AAT TGG GGC
CGG TGG TCG GAC AAA CTC TCA CCG TAG TTA ACC CCG
 A   T   S   L   F   E   S   G   I   N   W   G 580              590              600              610
  *                *                *                *
CGT GTG GTG GCT CTT CTG GGC TTC GGC TAC CGT CTG
GCA CAC CAC CGA GAA GAC CCG AAG CCG ATG GCA GAC
 R   V   V   A   L   L   G   F   G   Y   R   L 620              630              640              650
          *                *                *                *
GCC CTA CAC GTC TAC CAG CAT GGC CTG ACT GGC TTC
CGG GAT GTG CAG ATG GTC GTA CCG GAC TGA CCG AAG
 A   L   H   V   Y   Q   H   G   L   T   G   F

>SalI
             660              670       |    680
              *                *                *
CTA GGC CAG GTG ACC CGC TTC GTG GTC GAC TTC ATG
GAT CCG GTC CAC TGG GCG AAG CAC CAG CTG AAG TAC
 L   G   Q   V   T   R   F   V   V   D   F   M 690              700              710              720
      *                *                *                *
CTG CAT CAC TGC ATT GCC CGG TGG ATT GCA CAG AGG
GAC GTA GTG ACG TAA CGG GCC ACC TAA CGT GTC TCC
 L   H   H   C   I   A   R   W   I   A   Q   R
```

Fig. 3D

```
          730                 740                 750
           *                   *                   *
GGT GGC TGG GTG GCA GCC CTG AAC TTG GGC AAT GGT
CCA CCG ACC CAC CGT CGG GAC TTG AAC CCG TTA CCA
 G   G   W   V   A   A   L   N   L   G   N   G 760                 770                 780                 790
           *                   *                   *                   *
CCC ATC CTG AAC GTG CTG GTG GTT CTG GGT GTG GTT
GGG TAG GAC TTG CAC GAC CAC CAA GAC CCA CAC CAA
 P   I   L   N   V   L   V   V   L   G   V   V 800                 810                 820                 830
           *                   *                   *                   *
CTG TTG GGC CAG TTT GTG GTA CGA AGA TTC TTC AAA
GAC AAC CCG GTC AAA CAC CAT GCT TCT AAG AAG TTT
 L   L   G   Q   F   V   V   R   R   F   F   K 840                 850                 860
           *                   *                   *
TCA TGA C TCC CAA GGG TGC CCT TTG GGT CCC GGT TCA
AGT ACT G AGG GTT CCC ACG GGA AAC CCA GGG CCA AGT
 S   *
                    >Af12
          870             880 |          890                 900
           *               *  |           *                   *
GAC CCC TGC CTG GAC TTA AGC GAA GTC TTT GCC TTC
CTG GGG ACG GAC CTG AAT TCG CTT CAG AAA CGG AAG 910                 920                 930
           *                   *                   *
TCT GTT CCC TTG CAG GGT CCC CCC TCA AGA GTA CAG
AGA CAA GGG AAC GTC CCA GGG GGG AGT TCT CAT GTC

>Hind3
  |
  |
 940                950                 960                 970
  *|                  *                   *                   *
AAG CTT TAG CAA GTG TGC ACT CCA GCT TCG GAG GCC
TTC GAA ATC GTT CAC ACG TGA GGT CGA AGC CTC CGG
```

Fig. 3E

```
                                        >Pst1
                                          |
        980              990             1000            1010
         *                *                *               *
  CTG CGT GGG GGC CAG TCA GGC TGC AGA GGC ACC TCA
  GAC GCA CCC CCG GTC AGT CCG ACG TCT CCG TGG AGT

Apa1
           1020             1030            1040       |
            *                *               *
   ACA TTG CAT GGT GCT AGT GCC CTC TCT CTG GGC CCA
   TGT AAC GTA CCA CGA TCA CGG GAG AGA GAC CCG GGT 1050             1060            1070            1080
         *                *               *               *
   GGG CTG TGG CCG TCT CCT CCC TCA GCT CTC TGG GAC
   CCC GAC ACC GGC AGA GGA GGG AGT CGA GAG ACC CTG 1090             1100            1110
            *                *               *
   CTC CTT AGC CCT GTC TGC TAG GCG CTG GGG AGA CTG
   GAG GAA TCG GGA CAG ACG ATC CGC GAC CCC TCT GAC 1120             1130            1140            1150
         *                *               *               *
   ATA ACT TGG GGA GGC AAG AGA CTG GGA GCC ACT TCT
   TAT TGA ACC CCT CCG TTC TCT GAC CCT CGG TGA AGA 1160             1170            1180            1190
         *                *               *               *
   CCC CAG AAA GTG TTT AAC GGT TTT AGC TTT TTA TAA
   GGG GTC TTT CAC AAA TTG CCA AAA TCG AAA AAT ATT 1200             1210            1220
            *                *               *
   TAC CCT TGT GAG AGC CCA TTC CCA CCA TTC TAC CTG
   ATG GGA ACA CTC TCG GGT AAG GGT GGT AAG ATG GAC

Aha2
   1230    |    1240            1250            1260
    *                *               *               *
   AGG CCA GGA CGT CTG GGG TGT GGG GAT TGG TGG GTC
   TCC GGT CCT GCA GAC CCC ACA CCC CTA ACC ACC CAG
```

Fig. 3F

```
              1270                1280                1290
                *                   *                   *
        TAT GTT CCC CAG GAT TCA GCT ATT CTG GAA GAT CAG
        ATA CAA GGG GTC CTA AGT CGA TAA GAC CTT CTA GTC 1300            1310            1320            1330
          *               *               *               *
        CAC CCT AAG AGA TGG GAC TAG GAC CTG AGC CTG GTC
        GTG GGA TTC TCT ACC CTG ATC CTG GAC TCG GAC CAG 1340            1350            1360            1370
                *               *               *               *
        CTG GCC GTC CCT AAG CAT GTG TCC CAG GAG CAG GAC
        GAC CGG CAG GGA TTC GTA CAC AGG GTC CTC GTC CTG 1380            1390            1400
                  *               *               *
        CTA CTA GGA GAG GGG GGC CAA GGT CCT GCT CAA CTC
        GAT GAT CCT CTC CCC CCG GTT CCA GGA CGA GTT GAG 1410            1420            1430            1440
          *               *               *               *
        TAC CCC TGC TCC CAT TCC TCC CTC CGG CCA TAC TGC
        ATG GGG ACG AGG GTA AGG AGG GAG GCC GGT ATG ACG 1450            1460            1470
                *               *               *
        CTT TGC AGT TGG ACT CTC AGG GAT TCT GGG CTT GGG
        GAA ACG TCA ACC TGA GAG TCC CTA AGA CCC GAA CCC 1480            1490            1500            1510
          *               *               *               *
        GTG TGG GGT GGG GTG GAG TCG CAG ACC AGA GCT GTC
        CAC ACC CCA CCC CAC CTC AGC GTC TGG TCT CGA CAG 1520            1530            1540            1550
                *               *               *               *
        TGA ACT CAC GTG TCA GAA GCC TCC AAG CCT GCC TCC
        ACT TGA GTG CAC AGT CTT CGG AGG TTC GGA CGG AGG 1560            1570            1580
                  *               *               *
        CAA GGT CCT CTC AGT TCT CTC CCT TCC TCT CTC CTT
        GTT CCA GGA GAG TCA AGA GAG GGA AGG AGA GAG GAA
```

Fig. 3G

```
        1590              1600              1610              1620
         *                 *                 *                 *
ATA GAC ACT TGC TCC CAA CCC ATT CAC TAC AGG TGA
TAT CTG TGA ACG AGG GTT GGG TAA GTG ATG TCC ACT 1630              1640              1650
               *                 *                 *
AGG CTC TCA CCC ATC CCT GGG GGC CTT GGG TGA GTG
TCC GAG AGT GGG TAG GGA CCC CCG GAA CCC ACT CAC 1660              1670              1680              1690
       *                 *                 *                 *
GCC TGC TAA GGC TCC TCC TTG CCC AGA CTA CAG GGC
CGG ACG ATT CCG AGG AGG AAC GGG TCT GAT GTC CCG 1700              1710              1720              1730
         *                 *                 *                 *
TTA GGA CTT GGT TTG TTA TAT CAG GGA AAA GGA GTA
AAT CCT GAA CCA AAC AAT ATA GTC CCT TTT CCT CAT 1740              1750              1760
               *                 *                 *
GGG AGT TCA TCT GGA GGG TTC TAA GTG GGA GAA GGA
CCC TCA AGT AGA CCT CCC AAG ATT CAC CCT CTT CCT

>BamH1
        1770              1780              1790     |      1800
         *                 *                 *       |        *
CTA TCA ACA CCA CTA GGA ATC CCA GAG GTG GAT CCT
GAT AGT TGT GGT GAT CCT TAG GGT CTC CAC CTA GGA 1810              1820              1830
               *                 *                 *
CCC TCA TGG CTC TGG CAC AGT GTA ATC CAG GGG TGT
GGG AGT ACC GAG ACC GTG TCA CAT TAG GTC CCC ACA 1840              1850              1860              1870
         *                 *                 *                 *
AGA TGG GGG AAC TGT GAA TAC TTG AAC TCT GTT CCC
TCT ACC CCC TTG ACA CTT ATG AAC TTG AGA CAA GGG
```

Fig. 3H

```
         1880                1890                1900                1910
           *                   *                   *                   *
    CCA CCC TCC ATG CTC CTC ACC TGT CTA GGT CTC CTC
    GGT GGG AGG TAC GAG GAG TGG ACA GAT CCA GAG GAG 1920                1930                1940
           *                   *                   *
    AGG GTG GGG GGT GAC AGT GCC TTC TCT ATT GGC ACA
    TCC CAC CCC CCA CTG TCA CGG AAG AGA TAA CCG TGT 1950                1960                1970                1980
           *                   *                   *                   *
    GCC TAG GGT CTT GGG GGT CAG GGG GGA GAA GTT CTT
    CGG ATC CCA GAA CCC CCA GTC CCC CCT CTT CAA GAA 1990                2000                2010
                *                   *                   *
    GAT TCA GCC AAA TGC AGG GAG GGG AGG CAG ATG GAG
    CTA AGT CGG TTT ACG TCC CTC CCC TCC GTC TAC CTC 2020                2030                2040                2050
           *                   *                   *                   *
    CCC ATA GGC CAC CCC CTA TCC TCT GAG TGT TTG GAA
    GGG TAT CCG GTG GGG GAT AGG AGA CTC ACA AAC CTT 2060                2070                2080                2090
           *                   *                   *                   *
    ATA AAC TGT GCA ATC CCC TCA AAA AAA AAA CGG AGA
    TAT TTG ACA CGT TAG GGG AGT TTT TTT TTT GCC TCT

TCC
    AGG
```

Fig. 5A

```
              10                  20                  30
               *                   *                   *
TTT TAA TAT AAA TTA ATG TGC TCT ATT TAT AGA GAC
AAA ATT ATA TTT AAT TAC ACG AGA TAA ATA TCT CTG 40                  50                  60                  70
          *                   *                   *                   *
AAT ACA TGA AAT ATA CTT AAT AAA AAT TCA AAT GTT
TTA TGT ACT TTA TAT GAA TTA TTT TTA AGT TTA CAA 80                  90                 100
               *                   *                   *
ATA GAA CTG AAA AAG ATG AAA AGT AAA AAC AAC CTA
TAT CTT GAC TTT TTC TAC TTT TCA TTT TTG TTG GAT 110                 120                 130                 140
     *                   *                   *                   *
TTC CCC AGA GGT AGC CAC TGT CCA TAG TTT CTA TTT
AAG GGG TCT CCA TCG GTG ACA GGT ATC AAA GAT AAA 150                 160                 170                 180
          *                   *                   *                   *
TAG ATT CTT TCC TTT ATA CAA GAT TAT TAT AGC TTC
ATC TAA GAA AGG AAA TAT GTT CTA ATA ATA TCG AAG 190                 200                 210
               *                   *                   *
TAT TTT TTG GTG TAT GAA CTG TAG TCC TAG AGG ATT
ATA AAA AAC CAC ATA CTT GAC ATC AGG ATC TCC TAA 220                 230                 240                 250
     *                   *                   *                   *
TTA TTA GTT ATG AGT TCT ATA ACT AAG ATC CAT CAT
AAT AAT CAA TAC TCA AGA TAT TGA TTC TAG GTA GTA 260                 270                 280
          *                   *                   *
CTT AGT TGC TAA GAA CGT AGA TAC TGA GAA CAT CAT
GAA TCA ACG ATT CTT GCA TCT ATG ACT CTT GTA GTA
```

Fig. 5B

```
        290              300              310              320
         *                *                *                *
TTA AAA AAA CAT TTT TGG CTG GCA CCT CAT GAT CAC
AAT TTT TTT GTA AAA ACC GAC CGT GGA GTA CTA GTG 330              340              350              360
         *                *                *                *
TGG AGT CTC GCG GGT CCC TCA GGC TGC ACA GGG ACA
ACC TCA GAG CGC CCA GGG AGT CCG ACG TGT CCC TGT 370              380              390
              *                *                *
AGT AAA GGC TAC ATC CAG ATG CTG GGA ATG CAC TGA
TCA TTT CCG ATG TAG GTC TAC GAC CCT TAC GTG ACT 400              410              420              430
         *                *                *                *
CGC CCA TTC CTG GAA ACT GGG CTC CCA CTC AGC CCC
GCG GGT AAG GAC CTT TGA CCC GAG GGT GAG TCG GGG 440              450              460
              *                *                *
TGG GAG CAG CAG CCG CCA GCC CCT CGG GAC CTC CAT
ACC CTC GTC GTC GGC GGT CGG GGA GCC CTG GAG GTA 470              480              490              500
         *                *                *                *
CTC CAC CCT GCT GAG CCA CCC GGG TTG GGC CAG GAT
GAG GTG GGA CGA CTC GGT GGG CCC AAC CCG GTC CTA 510              520              530              540
         *                *                *                *
CCC GGC AGG CTG ATC CCG TCC TCC ACT GAG ACC TGA
GGG CCG TCC GAC TAG GGC AGG AGG TGA CTC TGG ACT 550              560              570
              *                *                *
AAA ATG GCT TCG GGG CAA GGC CCA GGT CCT CCC AGG
TTT TAC CGA AGC CCC GTT CCG GGT CCA GGA GGG TCC
     M   A   S   G   Q   G   P   G   P   P   R
```

Fig. 5C

```
           580                 590                 600                 610
            *                   *                   *                   *
CAG   GAG   TGC   GGA   GAG   CCT   GCC   CTG   CCC   TCT   GCT   TCT
GTC   CTC   ACG   CCT   CTC   GGA   CGG   GAC   GGG   AGA   CGA   AGA
 Q     E     C     G     E     P     A     L     P     S     A     S 620                 630                 640
                 *                   *                   *
GAG   GAG   CAG   GTA   GCC   CAG   GAC   ACA   GAG   GAG   GTT   TTC
CTC   CTC   GTC   CAT   CGG   GTC   CTG   TGT   CTC   CTC   CAA   AAG
 E     E     Q     V     A     Q     D     T     E     E     V     F 650                 660                 670                 680
   *                   *                   *                   *
CGC   AGC   TAC   GTT   TTT   TAC   CAC   CAT   CAG   CAG   GAA   CAG
GCG   TCG   ATG   CAA   AAA   ATG   GTG   GTA   GTC   GTC   CTT   GTC
 R     S     Y     V     F     Y     H     H     Q     Q     E     Q 690                 700                 710                 720
         *                   *                   *                   *
GAG   GCT   GAA   GGG   GCG   GCT   GCC   CCT   GCC   GAC   CCA   GAG
CTC   CGA   CTT   CCC   CGC   CGA   CGG   GGA   CGG   CTG   GGT   CTC
 E     A     E     G     A     A     A     P     A     D     P     E

>NcoI
              730                 740                 750   |
               *                   *                   *   |
ATG   GTC   ACC   TTA   CCT   CTG   CAA   CCT   AGC   AGC   ACC   ATG
TAC   CAG   TGG   AAT   GGA   GAC   GTT   GGA   TCG   TCG   TGG   TAC
 M     V     T     L     P     L     Q     P     S     S     T     M 760                 770                 780                 790
   *                   *                   *                   *
GGG   CAG   GTG   GGA   CGG   CAG   CTC   GCC   ATC   ATT   GGG   GAC
CCC   GTC   CAC   CCT   GCC   GTC   GAG   CGG   TAG   TAA   CCC   CTG
 G     Q     V     G     R     Q     L     A     I     I     G     D
```

Fig. 5D

```
800              810              820
 *                *                *
GAC ATC AAC CGA CGC TAT GAC TCA GAG TTC CAG ACC
CTG TAG TTG GCT GCG ATA CTG AGT CTC AAG GTC TGG
 D   I   N   R   R   Y   D   S   E   F   Q   T

>PstI
830              840       |     850              860
 *                *                *                *
ATG TTG CAG CAC CTG CAG CCC ACG GCA GAG AAT GCC
TAC AAC GTC GTG GAC GTC GGG TGC CGT CTC TTA CGG
 M   L   Q   H   L   Q   P   T   A   E   N   A 870              880              890              900
         *                *                *                *
TAT GAG TAC TTC ACC AAG ATT GCC TCC AGC CTG TTT
ATA CTC ATG AAG TGG TTC TAA CGG AGG TCG GAC AAA
 Y   E   Y   F   T   K   I   A   S   S   L   F 910              920              930
                 *                *                *
GAG AGT GGC ATC AAT TGG GGC CGT GTG GTG GCT CTT
CTC TCA CCG TAG TTA ACC CCG GCA CAC CAC CGA GAA
 E   S   G   I   N   W   G   R   V   V   A   L 940              950              960              970
         *                *                *                *
CTG GGC TTC AGC TAC CGT CTG GCC CTA CAC ATC TAC
GAC CCG AAG TCG ATG GCA GAC CGG GAT GTG TAG ATG
 L   G   F   S   Y   R   L   A   L   H   I   Y 980              990              1000
                 *                *                *
CAG CGT GGC CTG ACT GGC TTC CTG GGC CAG GTG ACC
GTC GCA CCG GAC TGA CCG AAG GAC CCG GTC CAC TGG
 Q   R   G   L   T   G   F   L   G   Q   V   T
```

Fig. 5E

```
     1010              1020              1030              1040
      *                 *                 *                 *
CGC TTT GTG GTG GAC TTC ATG CTG CAT CAC TGC ATT
GCG AAA CAC CAC CTG AAG TAC GAC GTA GTG ACG TAA
 R   F   V   V   D   F   M   L   H   H   C   I 1050              1060              1070              1080
      *                 *                 *                 *
GCC CGG TGG ATT GCA CAG AGG GGT GGC TGG GTG GCA
CGG GCC ACC TAA CGT GTC TCC CCA CCG ACC CAC CGT
 A   R   W   I   A   Q   R   G   G   W   V   A 1090              1100              1110
           *                 *                 *
GCC CTG AAC TTG GGC AAT GGT CCC ATC CTG AAC GTG
CGG GAC TTG AAC CCG TTA CCA GGG TAG GAC TTG CAC
 A   L   N   L   G   N   G   P   I   L   N   V 1120              1130              1140              1150
      *                 *                 *                 *
CTG GTG GTT CTG GGT GTG GTT CTG TTG GGC CAG TTT
GAC CAC CAA GAC CCA CAC CAA GAC AAC CCG GTC AAA
 L   V   V   L   G   V   V   L   L   G   Q   F 1160              1170              1180
           *                 *                 *
GTG GTA CGA AGA TTC TTC AAA TCA TGA CTC CCA AGG
CAC CAT GCT TCT AAG AAG TTT AGT ACT GAG GGT TCC
 V   V   R   R   F   F   K   S   *

1190              1200              1210              1220
  *                 *                 *                 *
GTG CCT TTG GGG TCC CAG TTC AGA CCC CTG CCT GGA
CAC GGA AAC CCC AGG GTC AAG TCT GGG GAC GGA CCT 1230              1240              1250              1260
           *                 *                 *                 *
CTT AAG CGA AGT CTT TGC CTT CTC TGC TCC TTG CAG
GAA TTC GCT TCA GAA ACG GAA GAG ACG AGG AAC GTC
```

Fig. 5F

```
                                      >Hind3
            1270              1280      |
             *                 *
GGT CCC CCC TCA AGA GTA CAG AAG CTT
CCA GGG GGG AGT TCT CAT GTC TTC GAA
```

```
cdn1        masgqgpgpprqecgepalpsaseeqvaqdteevfrsyvfyrhqqeeaegvaapadpemvt
cdn2        masgqgpgpprqecgepalpsaseeqvaqdteevfrsyvfyHhqqeeaegAaapadpemvt
bcl2                  mahagrtgyDNREIVMKYIHYKLSQRGYEWdagdvgaappgaapapgifssqpghtphtaasrdpvartsplqtpaapgaa
bax                                                                mdgsgeprgggptsseqimktgalllqgfiqdragrmggeap
bcl-x                        msqSNRELVVDFLSYKLSQKGYSWsqfsdveenrteapegtesemetpsaingnpswhladspavngatghsssl
mcl-1       ...(+123 aa)eldgyepeplgkrpaviplle1vgesGnntstdgslpstpppaeeedelyrqsle1isrylreqatgakdtk
A1                                                                                maeselmhihslaehylqyvlq
bhrf                                                                                                  megeeiyhniineilvgy
LMW5-HL                                                                   maystreillalcirdsrvhngtlhpvlelaar
ced9        mtrctadnsltnpayrrrtmatgemkeflgikgteptdfginsdaqdlpspsrqastrrmsigesidgkindweeprlDIEGFVVDYFTHRIRQNGMEWfgapg cdn1        lplqpsstmgQVGRQLAIIGDDINRRYDSEFQTMLQHLQPTAENAYEYFTKIATSLFESGI-NWGRVVALLGFYRLALHVYQHGLTGFLGQVTRFVVDFMLHH
cdn2        lplqpsstmgQVGRQLAIIGDDINRRYDSEFQTMLQHLQPTAENAYEYFTKIASSLFESGI-NWGRVVALLGFSYRLALHIYQRGLTGFLGQVTRFVVDFMLHH
bcl2        agpalspvppVVHLTLRQAGDDFSRRYRRDFAEMSRQLHLtpftargRFATVVEELFRDGV-NWGRIVAFFEFGVMCVESVNREMSPLVDNIALWMTEY-LNR
bax         elaldpvpqdastkklseclkrigdeldsnmelqrmiaavdtdsprevFFRVAADMFSDGNFNWGRVALFYFASKLVLKALCTKVPELIRTIMGWTLDF-LRE
bcl-x       darevipma-AVKQALREAGDEFELRYRRAFSDLTSQLHITPGTAYQSFEQVVNELFRDGV-NWGRIVAFFSFGGALCVESVDKEMQVLVSRIAAWMATY-LND
mcl-1       pmgrsgatsrkaIETLRRVGDGVQRNHETVFQGMLRKLDIKNEDDVKSLSRVMIHVFSDGVTNWGRIVTLISFGAFVAKHLKTINQESCIEPLAESITD-VLVR
A1          vpafesapsqacrvlqrvafsvqkeveknlksylddfhvesidtariiFNQVMEKEFEDGIINWGRIVTIFAFGGVLLKKLpqeqialdvcaykqvssfvaefi
bhrf        etplrlspedtvvlryhvlleeiiernsetftetwnrfithtehvdldfnsvfleifhD-LINWGRICGFIVFSARMAKYCKDAnn-HLESTVITTAYNF-SEG
LMW5-HL     ikyymndihelspyqqgikkiltyydeclnkqvtitfslnaqeiktQFTGVVTELFKrgdpslgralawmawcmhacrtlccnqstpyyvvdlsvrgmleaM-
ced9        lpcgvqpehemmrvmgtifekkhaenfetfceqLlavprisfslyqdvvrtvgnaqtdqcpMSYGRLIGLISFGGFVAAKMmesvelggqvrnlfvytslfIKT cdn1        CIAR--WIA-QR-GGWVAALNLGngpilnvlvvlgvvllgqfvvrrffks
cdn2        CIAR--WIA-QR-GGWVAALNLGngpilnvlvvlgvvllgqfvvrrffks
bcl2        HLHT--WI--QDNGGWDAFVELYgpsmrplfdfswlslktllslalvgacitlgaylghk
bax         RLLG--WI--QDQGGWDGLLSYFgtptwqtvtifvagvltasltiwkkmg
bcl-x       HLEP--WI--QENGGWDTFVELYgnnaaaesrkgqerfnrwfltgmtvagvvllgslfsrk
mcl-1       TKRD--WLVKQ--RGWDGFVEFFhvedleggirnvllafagvagvgaglaylir
A1          MNNTGEWI-RQ-NGGWEdgfikkfepksgwltflqmtgqiwemlfllk
bhrf        -LDG--WIHQQ--GGWStliednipgsrrfswtlflagltlsllvicsylfisrgrh
LMW5-HL     KHNLLPWMISH--GGQEEFLAFslhsqiysvifnikyflskfcnhhflrscvqlirkcnli
ced9        -RIRNNWKE-H--NRSWDDFMTLakqmkedyeraeaekvgrrkqnrrwsmigagvtagaiqivqvvvcgrmmfslk

SEQUENCE IDENTITY:

cdn1/cdn2 = 97%

FIG. 6
```

>EcoR1

```
                 *           *           *           *           *           *           *         80
                 *           *           *           *           *           *           *          *
GAATTCTGGT AATTAGTTAA ACAACCTTGA ACAAGTTGTT TCACTTCTCT GAGTCTCAGT TTCTCACTCA AAAATGGTGA

*           *           *           *           *           *           *         160
       *           *           *           *           *           *           *           *
ATAATTTGTA AGACTTCGCT AATAATCTAC GACTCTACAA GAGGCAATAG GGTACTGTGG ACAGAGAGCA GGCTTTGGAA
```

>Hind3
>Ba11

```
       *           *           *           *          *|         *           *         240
       *           *           *           *          *||        *           *           *
ACACACAAGA CTGGGTTTAG ATTCCTGCAC TCCACCCAGT GTGTGACTTG GCCAAGCTTC TTCACTTCTC TAAACCCCCA

*           *           *           *           *           *           *         320
       *           *           *           *           *           *           *           *
TCTGTGTATC TGTACAGGAA TGAATGAATG AGTATGTGCA GCCAAGCTAT GCAAACTCCA GGTTAAAATA TTGCCTTGGG
```

>Af12

```
       *           *           *           *           *          *|          *         400
       *           *           *           *           *          *|          *           *
TTTTTTAGTA AATTGTTCAA GCCCATGACA TTCTAGCAGA AAAAGCCTAG TGTCTCTTTC TTAAGGTGAT TGTGTCCATG

*           *           *           *           *           *           *         480
       *           *           *           *           *           *           *           *
TGTTTTCCAG GAACTCTATG GGTTTCTCAA CCCAAATTCA CCCTGCCCTT GACCAAATGG CTCACCAGCT TCACGGATGC
```

>Pst1                     >Pst1

```
       *          *|         *          *|          *           *           *         560
       *          *|         *          *|          *           *           *           *
TGCTCTGATG ACACACCCTG CAGTCAGCAT CTGCCCCTGC AGCTAGAATG GATTTCTGAG TGGGCATTAG CTGGGGGATA
```

>Bg12

```
       *          *|         *           *           *           *           *         640
       *          *|         *           *           *           *           *           *
CCACATGGGC ACCAATGTCA CAGATCTTCT GTCACAGTCC ACCCCGAACC ATTGCTTCTC AAATCATAAT CCCTTAGCAG
```

>Spe1

```
       *           *           *           *           *           *          *|       720
       *           *           *           *           *           *          *|         *
GACAGCTAGG TGCAGCACGC ATGACACAAA CACCAGCCCT TGCCTACAAT CTCAGCCACT ATCTTGAGTC TGAGCAACTA

*           *           *           *           *           *           *         800
       *           *           *           *           *           *           *           *
GTCTAGTGGC AGCCGCGCCC TTCCTTTTCA AGAGAGTTCT GGGATCAGAT CCTTTCACAA ACAGATCCCT CCCCACCCTG

*           *           *           *           *           *           *         880
       *           *           *           *           *           *           *           *
CCTGTTGTCC AGGTCTGCAC ACTGAAAAGT AAGACAGCAT TGCTAAGCC ATATTTCAAA AAGTTTGCTT ATACCTTCAT
```

FIG. 7A

```
                    >Afl2                                                               >Stul
                     |                                                                   |
         *          *|         *          *          *          *          *           |  9.0
                                                                                        |  *
CTCAGGACAA CAAGTGCCTG CTTAAGAGCC TTATGTTTGT GTAACTGGTA TTTTTTTTTC CCCTGACCTT CCAAGGCCTA 1040
         *          *          *          *          *          *          *            *
GTCTACTTTC TCCCTCCCTA GCTGAACAAA AGTGAAGTTG AAATAATTTG AACTACCCCT TTTAGTGGGC AGCCCATTTG 1120
         *          *          *          *          *          *          *            *
ATTTTTACCT TAGCCAGAGC CTTAATTTGT CCATGTGAGC ATAGCAGTAC CTTGCAGCAC CTGAGGCACA ATACATTGTT >Dral
 |
>Aha3                                                                          >Ncol
 |                                                                              |
 |       *          *          *          *          *          *          *    | 120:0
                                                                                |  *
TAAAGAGTGA CAGTGCGTCC CATTCCAATA AGAACCACAC TCAGAGCAAA GGTTCCCTCT CCTGTGTGGA GAGTGACC(A 1280
         *          *          *          *          *          *          *            *
TGGTAGAAAA TTTGCAGACT TCGTTACCTC TTCATCAGTT GAAAAATCTA TTTATTCATT TATGCATTTA ATTTTCCCTA >Pst1
                                                                     |
                                                                     |                   1360
         *          *          *          *          *          *   |      *            *
TCTAAGCCAG GGATAGTCAA ACATTTTCTG TAAAGGGCCA AGTAGCATGA TAAATATGTT AGGCTCTGCA GGCCACTTAC >Aha3
                                                           |
                                                          >Dral
                                                           |
                                                           |                              1440
         *          *          *          *          *    |*         *                   *
AGTTTTGTCA TGTATTCTTT TTTTGCTCCC TGTTTGTATT ATTTTGTTTA CAATGCTTTA AAAATGTAAA AAAACAGATG >Aha?
                                                                                  |
                                                                                  | 15/0
         *          *          *          *          *          *          *     |  *
ATCACTGGAG TCTCACGGGT CCCTCGGGCC ACACAGGGAC AAGCAAAGGC TACATCCAGA TACCAGAAAT GCACTGAC(C 1600
         *          *          *          *          *          *          *            *
CCGTTCCTGG AAGCTGGGCT CCCACTCAGC CCCTGGGAGC AGCAGCCTCC AGCCCCTTGG GACCTTCAAC TCCACCCTGC

*          *          *          *          *          *          *
TGACCCACGC GGGTTGAGCC AGCATCCCTG GAGGCTGACA CTGTCCTCCA CTGAGACCTG AAAA ATG GCA TCG GGG
                                                                       M   A   S   G>
```

FIG. 7B

```
     1680
      *              *              *              *              *              *              *
CAA GGC CCA GGG CCT CCC AGG CAG GAG TGC GGA AAG CCT GCC CTG CCC TCT GCT TCT GAG GAG CAG
 Q   G   P   G   P   P   R   Q   E   C   G   K   P   A   L   P   S   A   S   E   E   Q>

1760
      *         *              *              *              *              *              *
GTA GCC CAG GAC ATG GAG GGG TTT TCC GCA GCT ACG TTT TTT ACC ACC ATC AGC AGG AAC AGG AGG
 V   A   Q   D   M   E   G   F   S   A   A   T   F   F   T   T   I   S   R   N   R   R>

>Not1                                                                          >Ncol
           |                     1840                                                     |
      *    |    *         *         *         *              *              *              *  |
CTG AAG GGG CGG CCG CCC CTG CCG ACC CAG AGA TGG TCA CCT TGC CCC TCC AAC CTA GCA GCA CCA
 L   K   G   R   P   P   L   P   T   Q   R   W   S   P   C   P   S   N   L   A   A   P>

1920
      *              *              *              *         *              *              *
TGG GGC AGG TGG GAC GGC AGC TCG CCA TCA CCA GGA CGA CAT CAA CCG GCA CTA TGA CTTCGGAGT
 W   G   R   W   D   G   S   S   P   S   P   G   R   H   Q   P   A   L   *>

>Pst1    >Pst1                        >Sca1_
           |        |                            |
      *    |   *    |    *              *        |    *         2000
                                                                *              *              *
TCCAGACCAT GCTGCAGCAC CTGCAGCCCA CGGCAGAGAA CGCCTACGAG TACTTCACCA AGATCGCCTC CAGCCTGTTT

2080
      *              *              *              *              *              *              *
GAGAGTGGCA TCAACCGGGG CCGTGTGGTG GCTCTCCTGG GCTTCGGCTA CCGTCTGGTC CTACATGTCT ACCAGCACC

2160
      *              *              *              *              *              *              *
CTTGACTGGC TTCCTGGGCC TGGTGACCCG CTTCGTGGTC TTCATGCTGC AACAAGGCAT CGCCCGGTGG ATCTCGCAGA

2240
      *              *              *              *              *              *              *
GGGGCGGCTG GGTGGCAGCC CTGGACTTGG GCAATAGTCC CATCCTGAAC GTGCTGGTGG TTGTGGGTGT GGTTCTGCTG

>Pvu2
                                                                  2320              |
      *              *              *              *              *                 |   *
GGCCAGTTTG TGGTAAGAAG ATTCTTCAAA TCATGACTCC CAGGGGTGTC CTTTGGGGTC CCAGCTGTGA CCCCTGCCTG

>Af12
  |
  |                                                               2400
  |   *              *              *              *              *              *              *
GACTTAAGCC AAGTCTTTGC CTTCCCCACT CCCTTGCAGG GGTCACCCTT CAAAAGTACA GAAGCTCTAG CAAGTGTGC
```

FIG. 7C

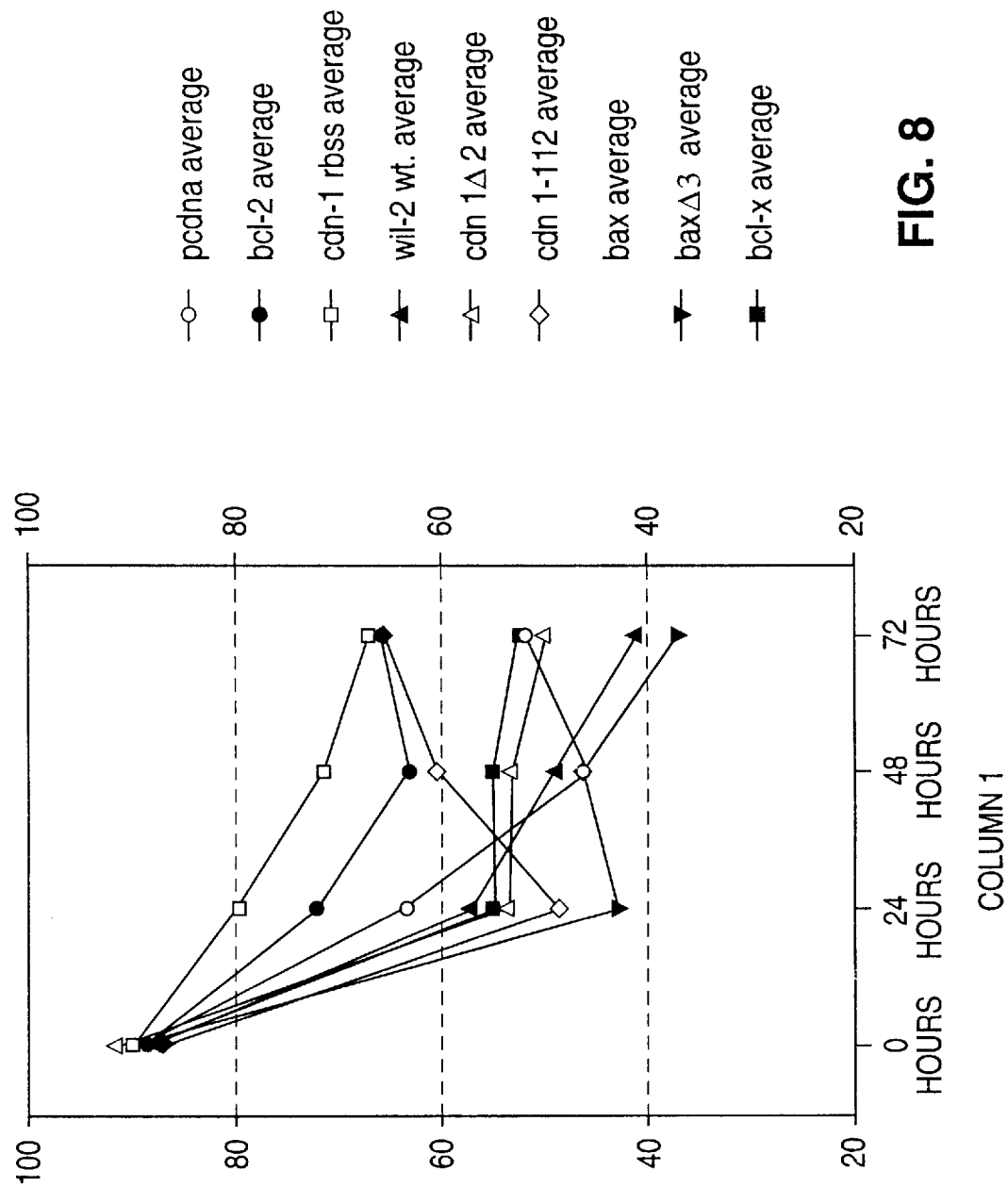

```
                                                              Δ1
MASGQGPGPPRQECGEPALPSASEEQVAQDTEEVFRSYVFYRHQQEQEAEGVAAPADPEMVT
                                                              ⊢→

Δ2                        Δ3
LPLQPSSTMGQVGRQLAIIGDDINRRYDSEFQTMLQHLQPTAENAYEYFTKIATSLFESGNWGR
    ⊢→                        ⊢→

VVALLGFGYRLALHVYQHGLTGFLGQVTRFVVDFMLHHCIARWIAQRGGWVAALNLGNGPILN

VLVVLGVVLLGQFVVRRFFKS
```

FIG. 11

APOPTOSIS-MODULATING PROTEINS, DNA ENCODING THE PROTEINS AND METHODS OF USE THEREOF

This application is a divisional of application Ser. No. 08/320,157 filed Oct. 7, 1994, which is a continuation-in-part of U.S. patent application Ser. No. 08/160,067 filed Nov. 30, 1993 now abandoned.

FIELD OF THE INVENTION

This invention relates to novel proteins with apoptosis-modulating activity, recombinant DNA encoding the proteins, compositions containing the proteins and methods of use thereof.

BACKGROUND OF THE INVENTION

Apoptosis is a normal physiologic process that leads to individual cell death. This process of programmed cell death is involved in a variety of normal and pathogenic biological events and can be induced by a number of unrelated stimuli. Changes in the biological regulation of apoptosis also occur during aging and are responsible for many of the conditions and diseases related to aging. Recent studies of apoptosis have implied that a common metabolic pathway leading to cell death may be initiated by a wide variety of signals, including hormones, serum growth factor deprivation, chemotherapeutic agents, ionizing radiation and infection by human immunodeficiency virus (HIV). Wyllie (1980) Nature, 284:555–556; Kanter et al. (1984) Biochem. Biophys. Res. Commun. 118:392–399; Duke and Cohen (1986) Lymphokine Res. 5:289–299; Tomei et al. (1988) Biochem. Biophys. Res. Commun. 155:324–331; Kruman et al. (1991) J. Cell. Physiol. 148:267–273; Ameisen and Capron (1991) Immunology Today 12:102; and Sheppard and Ascher (1992) J. AIDS 5:143. Agents that modulate the biological control of apoptosis thus have therapeutic utility in a wide variety of conditions.

Apoptotic cell death is characterized by cellular shrinkage, chromatin condensation, cytoplasmic blebbing, increased membrane permeability and interchromosomal DNA cleavage. Kerr et al. (1992) FASEB J. 6:2450; and Cohen and Duke (1992) Ann. Rev. Immunol. 10:267. The blebs, small, membrane-encapsulated spheres that pinch off of the surface of apoptotic cells, may continue to produce superoxide. radicals which damage surrounding cell tissue and may be involved in inflammatory processes.

Bcl-2 was discovered at the common chromosomal translocation site t(14:18) in follicular lymphomas and results in aberrant over-expression of bcl-2. Tsujimoto et al. (1984) Science 226:1097–1099; and Cleary et al. (1986) Cell 47:19–28. The normal function of bcl-2 is the prevention of apoptosis; unregulated expression of bcl-2 in B cells is thought to lead to increased numbers of proliferating B cells which may be a critical factor in the development of lymphoma. McDonnell and Korsmeyer (1991) Nature 349:254–256; and, for review see, Edgington (1993) Bio/Tech. 11:787–792. Bcl-2 is also capable of blocking of γ irradiation-induced cell death. Sentman et al. (1991) Cell 67:879–888; and Strassen (1991) Cell 67:889–899. It is now known that bcl-2 inhibits most types of apoptotic cell death and is thought to function by regulating an antioxidant pathway at sites of free radical generation. Hockenbery et al. (1993) Cell 75:241–251.

While apoptosis is a normal cellular event, it can also be induced by pathological conditions and a variety of injuries. Apoptosis is involved in a wide variety of conditions including but not limited to, cardiovascular disease, cancer regression, immunoregulation, viral diseases, anemia, neurological disorders, gastrointestinal disorders, including but not limited to, diarrhea and dysentery, diabetes, hair loss, rejection of organ transplants, prostate hypertrophy, obesity, ocular disorders, stress and aging.

Bcl-2 belongs to a family of proteins some of which have been cloned and sequenced. Williams and Smith (1993) Cell 74:777–779. All references cited herein, both supra and infra, are hereby incorporated by reference herein.

SUMMARY OF THE INVENTION

Substantially purified DNA encoding novel bcl-2 homologs, termed cdn-1, cdn-2 and cdn-3, as well as recombinant cells and transgenic animals expressing the cdn-1 and cdn-2 genes are provided. The substantially purified CDN-1 and CDN-2 proteins and compositions thereof are also provided. Diagnostic and therapeutic methods utilizing the DNA and proteins are also provided. Methods of screening for pharmaceutical agents that stimulate, as well as pharmaceutical agents that inhibit cdn-1 and cdn-2 activity levels are also provided.

BRIEF DESCRIPTION OF THE DRAWINGS

FIG. 1 (SEQ ID NO:1 through SEQ ID NO:5) depicts the PCR primers used to isolate the cdn-1 probes.

FIG. 3 (SEQ ID NO:6 and SEQ ID NO:7) depicts the nucleotide sequence of cdn-1.

FIG. 5 (SEQ ID NO:8 and SEQ ID NO:9) shows the sequence of the cdn-2 cDNA and flanking sequences and the corresponding predicted amino acid sequence of the cdn-2 protein.

FIG. 6 (SEQ ID NO:10 through SEQ ID NO:19) shows a comparison of N-terminal amino acid sequences of cdn-1, cdn-2 and known bcl-2 family members.

FIG. 7 (SEQ ID NO:20 and SEQ ID NO:21) shows the nucleotide sequence of cdn-3.

FIG. 8 shows the anti-apoptotic effects of cdn-1 and some of its derivatives in serum-deprivation induced apoptosis of WIL-2 cells.

FIG. 11 (SEQ ID NO:22) depicts the cdn-1 derivative proteins Δ1, Δ2 and Δ3. The N-terminal residues are indicated by the arrows. The remainder of the derivative proteins is the same as full-length cdn-1.

DETAILED DESCRIPTION OF THE INVENTION

The present invention encompasses substantially purified nucleotide sequences encoding the novel bcl-2 homologs, cdn-1 and cdn-2; and the proteins encoded thereby; compositions comprising cdn-1 and cdn-2 genes and proteins and methods of use of thereof. Note that in copending United States patent application Ser. No. 08/160,067, cdn-1 was termed cdi-1; although the name has been changed, the nucleotide sequence remains identical. The invention further includes recombinant cells and transgenic animals expressing the cloned cdn-1 or cdn-2 genes. The nucleotide and predicted amino acid residue sequences of cdn-1 are shown in FIG. 3; and those of cdn-2 are shown in FIG. 5. It has now been found that the proteins encoded by the cdn genes are capable of modulating apoptosis. In a lymphoblastoid cell line, cdn-1 was shown to decrease Fas-mediated apoptosis. In a mouse progenitor B cell line, FL5.12, cdn-2 and a derivative of cdn-1 decrease IL-3-induced apoptosis whereas cdn-1 slightly increased apoptosis. Thus, depending on the cell type, the derivative of cdn and the method of induction of apoptosis, apoptosis can be modulated in a highly specific manner by controlling the concentration of cdns.

Figure 2:
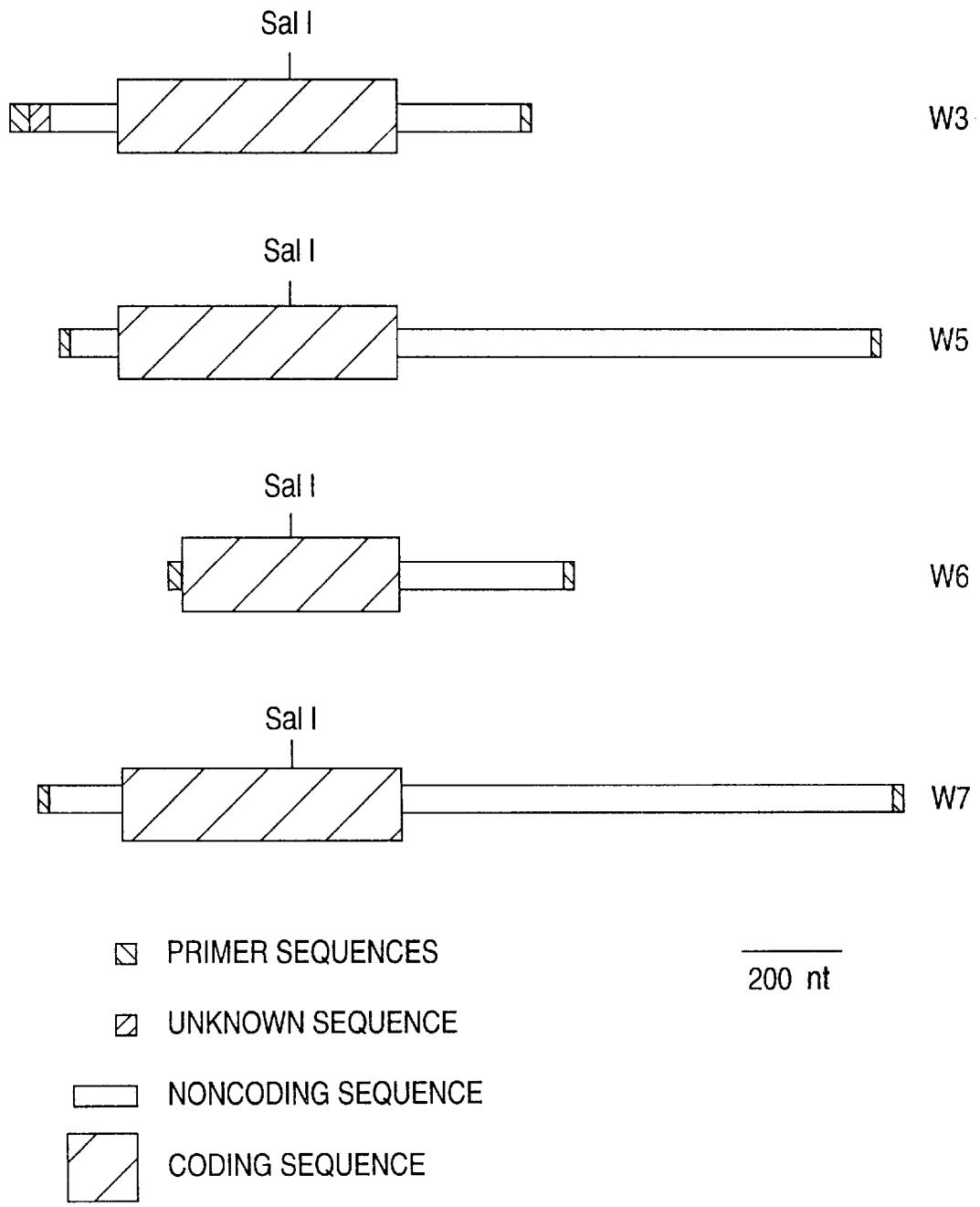
FIG. 2 depicts the cdn-1 clones obtained by the methods described in Example 1.

As used herein, "cdns" or "cdn" refers to the nucleic acid molecules described herein (cdn-1, cdn-2, cdn-3 and derivatives thereof), "the CDNs" or "CDN" refers to the proteins encoded thereby (CDN-1, CDN-2, CDN-3 and derivatives thereof). The present invention encompasses cdn-1 and cdn-2 nucleotide sequences. The cdn nucleotides include, but are not limited to, the cDNA, genome-derived DNA and synthetic or semi-synthetic DNA or RNA. The nucleotide sequence of the cdn-1 cDNA with the location of restriction endonuclease sites is shown in FIG. 2. As described in the examples herein, cdn-1 mRNA has been detected in a variety of human organs and tissues by Northern blot analysis. These organs include liver; heart; skeletal muscle; lung; kidney; and pancreas as shown in FIG. 3.

Similarly, cdn-2, cdn cDNA, genomic DNA and synthetic or semi-synthetic DNAs and RNAs are additional embodiments of the present invention. The nucleotide sequence of cdn-2 cDNA, along with the predicted amino acid sequence of cdn-2 protein and the locations-of restriction endonuclease recognition sites, is given in FIG. 5. The examples presented herein indicate that cdn-1 is on human chromosome 6 and that cdn-2 is on human chromosome 20. There is also a member of the family cdn-3 which is on human chromosome 11. Fluorescence in situ hybridization (FISH) indicated an approximate location of cdn-1 to be at 6p21–23. Within this region resides the gene for spinocerebellar ataxia type 1. Interestingly, apoptosis has been proposed recently to be involved in the related genetic disorder ataxia telangiectasia. Taken together with the chromosomal localization and the expression of cdn-1 in brain tissue, this suggests the possibility that cdn-1/cdn-2 might represent the SCAL gene locus. It is possible that cdn-2 and cdn-3 are pseudogenes. While these may not be expressed endogenously, they are capable of expression from a recombinant vector providing the appropriate promoter sequences. Thus, both cdn-2 and cdn-3 genes are encompassed by the present invention as are recombinant constructs thereof and proteins encoded thereby.

Figure 10:
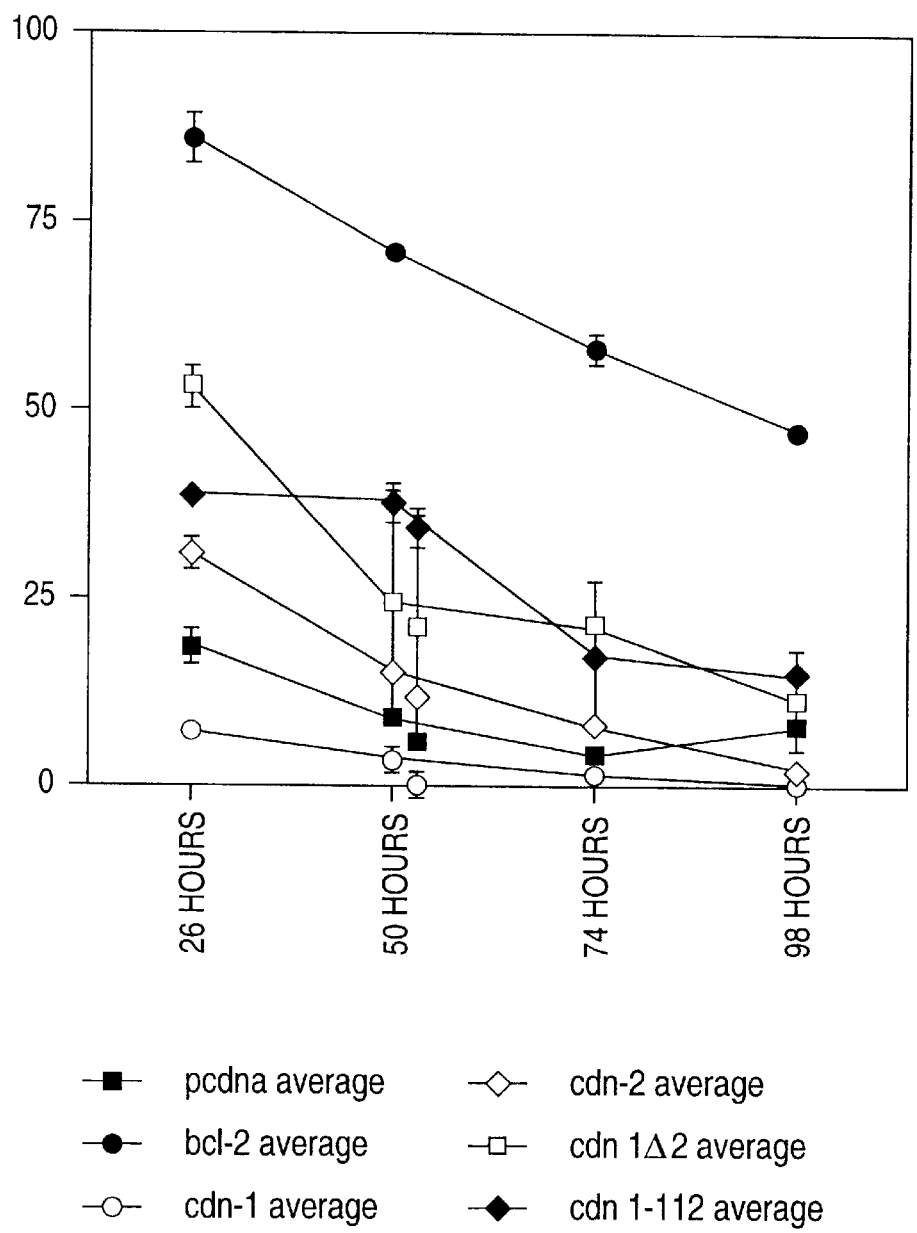
FIG. 10 shows modulation of apoptosis by cdn-1 and cdn-2 in FL5.12 cells.

Derivatives of the genes and proteins include any portion of the protein, or gene encoding the protein, which retains apoptosis modulating activity. FIG. 10 depicts three such derivatives of cdn-1 which have been shown to retain apoptosis-modulating activity. These derivatives, cdn1-Δ1, cdn1-Δ2 and cdn1-Δ3, are encompassed by the present invention.

The invention includes modifications to cdn DNA sequences such as deletions, substitutions and additions particularly in the non-coding regions of genomic DNA. Such changes are useful to facilitate cloning and modify gene expression.

Various substitutions can be made within the coding region that either do not alter the amino acid residues encoded or result in conservatively substituted amino acid residues. Nucleotide substitutions that do not alter the amino acid residues encoded are useful for optimizing gene expression in different systems. Suitable substitutions are known to those of skill in the art and are made, for instance, to reflect preferred codon usage in the particular expression systems.

The invention encompasses functionally equivalent variants and derivatives of cdns which may enhance, decrease or not significantly affect the properties of CDNs. For instance, changes in the DNA sequence that do not change the encoded amino acid sequence, as well as those that result in conservative substitutions of amino acid residues, one or a few amino acid deletions or additions, and substitution of amino acid residues by amino acid analogs are those which will not significantly affect its properties.

Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. Any conservative amino acid substitution which does not significantly affect the properties of CDNs is encompassed by the present invention.

Techniques for nucleic acid manipulation useful for the practice of the present invention are described in a variety of references, including but not limited to, *Molecular Cloning: A Laboratory Manual*, 2nd ed., Vol. 1–3, eds. Sambrook et al. Cold Spring Harbor Laboratory Press (1989); and *Current Protocols in Molecular Biology*, eds. Ausubel et al., Greene Publishing and Wiley-Interscience: New York (1987) and periodic updates.

The invention further embodies a variety of DNA vectors having cloned therein the cdn nucleotide sequences encoding. Suitable vectors include any known in the art including, but not limited to, those for use in bacterial, mammalian, yeast and insect expression systems. Specific vectors are known in the art and need not be described in detail herein.

The vectors may also provide inducible promoters for expression of the cdns. Inducible promoters are those which do not allow constitutive expression of the gene but rather, permit expression only under certain circumstances. Such promoters may be induced by a variety of stimuli including, but not limited to, exposure of a cell containing the vector to a ligand, metal ion, other chemical or change in temperature.

These promoters may also be cell-specific, that is, inducible only in a particular cell type and often only during a specific period of time. The promoter may further be cell cycle specific, that is, induced or inducible only during a particular stage in the cell cycle. The promoter may be both cell type specific and cell cycle specific. Any inducible promoter known in the art is suitable for use in the present invention.

The invention further includes a variety of expression systems transfected with the vectors. Suitable expression systems include but are not limited to bacterial, mammalian, yeast and insect. Specific expression systems and the use thereof are known in the art and are not described in detail herein.

The invention encompasses ex vivo transfection with cdns, in which cells removed from animals including man are transfected with vectors encoding CDNs and reintroduced into animals. Suitable transfected cells include individual cells or cells contained within whole tissues. In addition, ex vivo transfection can include the transfection of cells derived from an animal other than the animal or human subject into which the cells are ultimately introduced. Such grafts include, but are not limited to, allografts, xenografts, and fetal tissue transplantation.

Essentially any cell or tissue type can be treated in this manner. Suitable cells include, but are not limited to, cardiomyocytes and lymphocytes. For instance, lymphocytes, removed, transfected with the recombinant DNA and reintroduced into an HIV-positive patient may increase the half-life of the reintroduced T cells.

As an example, in treatment of HIV-infected patients by the above-described method, the white blood cells are removed from the patient and sorted to yield the $CD4^+$ cells. The $CD4^+$ cells are then transfected with a vector encoding CDNs and reintroduced into the patient. Alternatively, the unsorted lymphocytes can be transfected with a recombinant vector having at least one cdn under the control of a cell-specific promoter such that only $CD4^+$ cells express the cdn genes. In this case, an ideal promoter would be the CD4 promoter; however, any suitable $CD4^+$ T cell-specific promoter can be used.

Further, the invention encompasses cells transfected in vivo by the vectors. Suitable methods of in vivo transfection are known in the art and include, but are not limited to, that described by Zhu et al. (1993) Science 261:209–211. In vivo transfection by cdns may be particularly useful as a prophylactic treatment for patients suffering from atherosclerosis. Elevated modulation of the levels of CDN could serve as a prophylaxis for the apoptosis-associated reperfusion damage that results from cerebral and myocardial infarctions. In these patients with a high risk-of stroke and heart attack, the apoptosis and reperfusion damage associated with arterial obstruction could be prevented or at least mitigated.

Infarctions are caused by a sudden insufficiency of arterial or venous blood supply due to emboli, thrombi, or pressure that produces a macroscopic area of necrosis; the heart, brain, spleen, kidney, intestine, lung and testes are likely to be affected. Apoptosis occurs to tissues surrounding the infarct upon reperfusion of blood to the area; thus, modulation of CDN levels, achieved by a biological modifier-induced change in endogenous production or by in vivo transfection, could be effective at reducing the severity of damage caused by heart attacks and stroke.

Transgenic animals containing the recombinant DNA vectors are also encompassed by the invention. Methods of making transgenic animals are known in the art and need not be described in detail herein. For a review of methods used to make transgenic animals, see, e.g. PCT publication no. WO 93/04169. Preferably, such animals express recombinant cdns under control of a cell-specific and, even more preferably, a cell cycle specific promoter.

In another embodiment, diagnostic methods are provided to detect the expression of cdns either at the protein level or the mRNA level. Any antibody that specifically recognizes CDNs is suitable for use in CDN diagnostics. Abnormal levels of CDNs are likely to be found in the tissues of patients with diseases associated with inappropriate apoptosis; diagnostic methods are therefore useful for detecting and monitoring biological conditions associated with such apoptosis defects. Detection methods are also useful for monitoring the success of CDN-related therapies.

Purification or isolation of CDNs expressed either by the recombinant DNA or from biological sources such as tissues can be accomplished by any method known in the art. Protein purification methods are known in the art. Generally, substantially purified proteins are those which are free of other, contaminating cellular substances, particularly proteins. Preferably, the purified CDNs are more than eighty percent pure and most preferably more than ninety-five percent pure. For clinical use as described below, the CDNs are preferably highly purified, at least about ninety-nine percent pure, and free of pyrogens and other contaminants.

Suitable methods of protein purification are known in the art and include, but are not limited to, affinity chromatography, immunoaffinity chromatography, size exclusion chromatography, HPLC and FPLC. Any purification scheme that does not result in substantial degradation of the protein is suitable for use in the present invention.

The invention also includes the substantially purified CDNs having the amino acid residue sequences depicted in FIGS. 3 and 5, respectively. The invention encompasses functionally equivalent variants of CDNs which do not significantly affect their properties and variants which retain the same overall amino acid sequence but which have enhanced or decreased activity. For instance, conservative substitutions of amino acid residues, one or a few amino acid deletions or additions, and substitution of amino acid residues by amino acid analogs are within the scope of the invention.

Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. Any conservative amino acid substitution which does not significantly affect the properties of CDNs is encompassed by the present invention.

Suitable antibodies are generated by using the CDNs as an antigen or, preferably, peptides encompassing the CDN regions that lack substantial homology to the other gene products of the bcl family. Methods of detecting proteins using antibodies and of generating antibodies using proteins or synthetic peptides are known in the art and are not be described in detail herein.

CDN protein expression can also be monitored by measuring the level of cdn mRNA. Any method for detecting specific mRNA species is suitable for use in this method. This is easily accomplished using the polymerase chain reaction (PCR). Preferably, the primers chosen for PCR correspond to the regions of the cdn genes which lack substantial homology to other members of the bcl gene family. Alternatively, Northern blots can be utilized to detect cdn mRNA by using probes specific to cdns. Methods of utilizing PCR and Northern blots are known in the art and are not described in detail herein.

Methods of treatment with cdns also include modulating cellular expression of cdns by increasing or decreasing levels of cdn mRNA or protein. Suitable methods of increasing cellular expression of cdn include, but are not limited to, increasing endogenous expression and transfecting the cells with vectors encoding cdns. Cellular transfection is discussed above and is known in the art. Suitable indications for increasing endogenous levels of cdn include, but are not limited to, malignancies and cardiac-specific over-expression. Cardiac specific over-expression is particularly suitable for use in indications including, but not limited to, patients susceptible to heart disease and in advance of cardiotoxic therapies including, but not limited to, chemotherapies such as adriamycin, so as to offer cardioprotection.

In addition, increasing endogenous expression of cdns can be accomplished by exposing the cells to biological modifiers that directly or indirectly increase levels of CDNs either by increasing expression or by decreasing degradation of cdn mRNA. Suitable biological modifiers include, but are not limited to, molecules and other cells. Suitable molecules include, but are not limited to, drugs, cytokines, small molecules, hormones, combinations of interleukins, lectins and other stimulating agents e.g. PMA, LPS, bispecific antibodies and other agents which modify cellular functions or protein expression. Cells are exposed to such biological modifiers at physiologically effective concentrations, and the expression of cdns is measured relative to a control not exposed to the biological modifiers. Those biological modifiers which increase expression of cdns relative to the control are selected for further study.

The invention further encompasses a method of decreasing endogenous levels of cdns. The methods of decreasing endogenous levels of cdns include, but are not limited to, antisense nucleotide therapy and down-regulation of expression by biological modifiers. Antisense therapy is known in the art and its application will be apparent to one of skill in the art.

Screening for therapeutically effective biological modifiers is done by exposing the cells to biological modifiers which may directly or indirectly decrease levels of CDNs either by decreasing expression or by increasing the half-life of cdn mRNA or CDNs. Suitable biological modifiers include, but are not limited to, molecules and other cells. Suitable molecules include, but are not limited to, drugs, cytokines, small molecules, hormones, combinations of interleukins, lectins and other stimulating agents e.g. PMA, LPS, bispecific antibodies and other agents which modify cellular functions or protein expression. Cells are grown under conditions known to elicit expression of at least one cdn (preferably cdn-1), exposed to such biological modifiers at physiologically effective concentrations, and the expression of cdns is measured relative to a control not exposed to biological modifiers. Those biological modifiers which decrease the expression of cdns relative to a control are selected for further study. Cell viability is also monitored to ensure that decreased cdn expression is not due to cell death.

In determining the ability of biological modifiers to modulate (increase or decrease) cdn expression, the levels of endogenous expression may be measured or the levels of recombinant fusion proteins under control of cdn-specific promoter sequences may be measured. The fusion proteins are encoded by reporter genes.

Reporter genes are known in the art and include, but are not limited to chloramphenicol acetyl transferase (CAT) and β-galactosidase. Expression of cdn-1 and -2 can be monitored as described above either by protein or mRNA levels. Expression of the reporter genes can be monitored by enzymatic assays, or antibody-based assays, like ELISAs and RIAs, also known in the art. Potential pharmaceutical agents can be any therapeutic agent or chemical known to the art, or any uncharacterized compounds derived from natural sources such as fungal broths and plant extracts. Preferably, suitable pharmaceutical agents are those lacking substantial cytotoxicity and carcinogenicity.

Suitable indications for modulating endogenous levels of cdns are any in which cdn-mediated apoptosis is involved. These include, but are not limited to, various types of malignancies and other disorders resulting in uncontrolled cell growth such as eczema, or deficiencies in normal programmed cell death such as malignancies, including, but not limited to, B cell lymphomas.

The invention also encompasses therapeutic methods and compositions involving treatment of patients with biological modifiers to increase or decreast expression of cdns. Effective concentrations and dosage regimens may be empirically derived. Such derivations are within the skill of those in the art and depend on, for instance, age, weight and gender of the patient and severity of the disease. Alternatively, patients may be directly treated with either native or recombinant CDNs. The CDNs should be substantially pure and free of pyrogens. It is preferred that the recombinant CDNs be produced in a mammalian cell line so as to ensure proper glycosylation. CDNs may also be produced in an insect cell line and will be glycosylated.

For therapeutic compositions, a therapeutically effective amount of substantially pure CDN is suspended in a physiologically accepted buffer including, but not limited to, saline and phosphate buffered saline (PBS) and administered to the patient. Preferably administration is intravenous. Other methods of administration include but are not limited to, subcutaneous, intraperitoneal, gastrointestinal and directly to a specific organ, such as intracardiac, for instance, to treat cell death related to myocardial infarction.

Suitable buffers and methods of administration are known in the art. The effective concentration of a CDN will need to be determined empirically and will depend on the type and severity of the disease, disease progression and health of the patient. Such determinations are within the skill of one in the art.

Bcl-2 is thought to function in an antioxidant pathway. Veis et al. (1993) *Cell* 75:229–240. Therefore, therapy involving CDNs is suitable for use in conditions in which superoxide is involved. Administration of CDNs results in an increased extracellular concentration of CDNs, which is thought to provide a method of directly inhibiting superoxide accumulation that may be produced by the blebs associated with apoptosis. The therapeutic method thus includes, but is not limited to, inhibiting superoxide mediated cell injury.

Suitable indications for therapeutic use of CDNs are those involving free radical mediated cell death and include, but are not limited to, conditions previously thought to be treatable by superoxide dismutase. Such indications include but are not limited to HIV infection, autoimmune diseases, cardiomyopathies, neuronal disorders, hepatitis and other liver diseases, osteoporosis, and shock syndromes, including, but not limited to, septicemia.

Hybridization of cloned cdn DNA to messenger mRNA from various regions of the brain indicated high levels of expression of cdn-1 in each of the regions studied (FIG. 8). Therefore, neurological disorders are another area in which therapeutic applications of CDNs may be indicated.

The following examples are provided to illustrate but not limit the present invention. Unless otherwise specified, all cloning techniques were essentially as described by Sambrook et al. (1989) and all reagents were used according to the manufacturer's instructions.

EXAMPLE 1

Identification and Cloning of cdn-1 cDNA

An amino acid sequence comparison of the six known bcl-2 family members (FIG. 6) revealed two regions with considerable sequence identity, namely amino acids 144–150 and 191–199. In an attempt to identify new bcl-2 family members, degenerate PCR primers based on sequences in these regions were designed (FIG. 1) and PCR was performed using human heart cDNA and human B lymphoblastoid cell line (WIL-2) cDNA. PCR was performed using the Hot Start/Ampliwax technique (Perkin Elmer Cetus). The final concentration of the PCR primers and the template cDNA were 4 μM and 0.1–0.2 ng/ml, respectively. The conditions for cDNA synthesis were identical to those for first strand cDNA synthesis of the cDNA library as described below. PCR was performed in a Perkin Elmer Cetus DNA Thermal Cycler according to the method described by Kiefer et al. (1991) Biochem. Biophys. Res. Commun. 176:219–225, except that the annealing and extension temperatures during the first 10 cycles were 36° C. Following PCR, samples were treated with 5 units of DNA polymerase I, Klenow fragment for 30 min at 37° C. and then fractionated by electrophoresis on a 7% polyacrylamide, 1× TBE (Tris/borate/EDTA) gel. DNA migrating between 170–210 base pars was excised from the gel, passively eluted for 16 hours with gentle shaking in 10 mM Tris-HCl pH 7.5, 1 mM EDTA (TE), purified by passage over an Elutip-D column (Schleicher and Schuell), ligated to the pCR-Script vector (Stratagene) and transformed into Escherichia coli strain XL1-Blue MRF (Stratagene). Plasmid DNA from transformants (white colonies) containing both the heart and WIL-2 PCR products was isolated using the Magic Miniprep DNA Purification System (Promega), and the DNA inserts were sequenced by the dideoxy chain termination method according to Sanger et al. (1977) Proc. Natl. Acad. Sci. USA 74:5463–5467 (USB, Sequenase version 2.0). DNA sequence analysis of the eleven heart PCR products revealed two sequences identical to bcl-x (Boise et al. (1993) Cell 74:597–608) and ten other sequences unrelated to the bcl-2 family.

DNA sequence analyses of the eleven WIL-2 PCR products yielded one bcl-x sequence, five sequences identical to another bcl-2 family member, bax (Oldvai et al. (1993) Cell 74:609–619), four unrelated sequences and one novel bcl-2 related sequence, termed cdn-1. The unique cdn-1 amino acid sequence encoded by the PCR product is shown in FIG. 6 from amino acid 151–190 (top row).

To isolate the cdn-1 cDNA, a human heart cDNA library (Clontech) and a WIL-2 cDNA library, constructed as described by Zapf et al. (1990) J. Biol. Chem. 265:14892–14898 were screened using the cdn-1 PCR DNA insert as a probe. The DNA was $^{32}$P-labeled according to the method described by Feinberg and Vogelstein (1984) Anal. Biochem. 137:266–267 and used to screen 150,000 recombinant clones from both libraries according to the method described by Kiefer et al. (1991). Eight positive clones from the WIL-2 cDNA library and two positive clones from the heart cDNA library were identified. Four clones from the WIL-2 cDNA library and two from the heart cDNA library were further purified and plasmid DNA containing the cDNA inserts was excised from the λZAPII vector (Stratagene) (FIG. 2). The two longest clones, W7 (2.1 kb) and W5 (2.0 kb) were sequenced and shown to contain the cdn-1 probe sequence, thus confirming their authenticity. The heart cDNAs also encoded cdn-1.

The W7 DNA sequence along with the deduced amino acid residue sequence is shown in FIG. 2. The deduced amino acid sequence of cdn-1 was also aligned for maximum sequence identity with the other bcl-2 family members and is shown in FIG. 6. As can be seen, there is considerable sequence identity between cdn-1 and other family members between amino acids 100 and 200. Beyond this central region, sequence conservation falls off sharply. Like bcl-2, cdn-1 appears to be an intracellular protein in that it does not contain a either a hydrophobic signal peptide or N-linked glycosylation sites. Cdn-1 does contain a hydrophobic C-terminus that is also observed with all bcl-2 family members except LMW5-HL, suggesting its site of anti-apoptotic activity, like that of bcl-2, is localized to a membrane bound organelle such as the mitochondrial membrane, the endoplasmic reticulum or the nuclear membrane. Hockenbery et al. (1990); Chen-Levy et al. (1989) Mol. Cell. Biol. 9:701–710; Jacobsen et al. (1993) Nature 361:365–369; and Monighan et al. (1992) J. Histochem. Cytochem. 40:1819–1825.

EXAMPLE 2

Northern Blot Analysis of cDNA Clones

Northern blot analysis was performed according to the method described by Lehrach et al. (1977) Biochem. 16:4743–4651 and Thomas (1980) Proc. Natl. Acad. Sci. USA 77:5201–5205. In addition, a human multiple tissue Northern blot was purchased from Clontech. The coding regions of bcl-2 and cdn-1 cDNAs were labeled by the random priming method described by Feinberg and Vogelstein (1984) Anal. Biochem. 137:266–267. Hybridization and washing conditions were performed according to the methods described by Kiefer et al. (1991).

Figure 4:
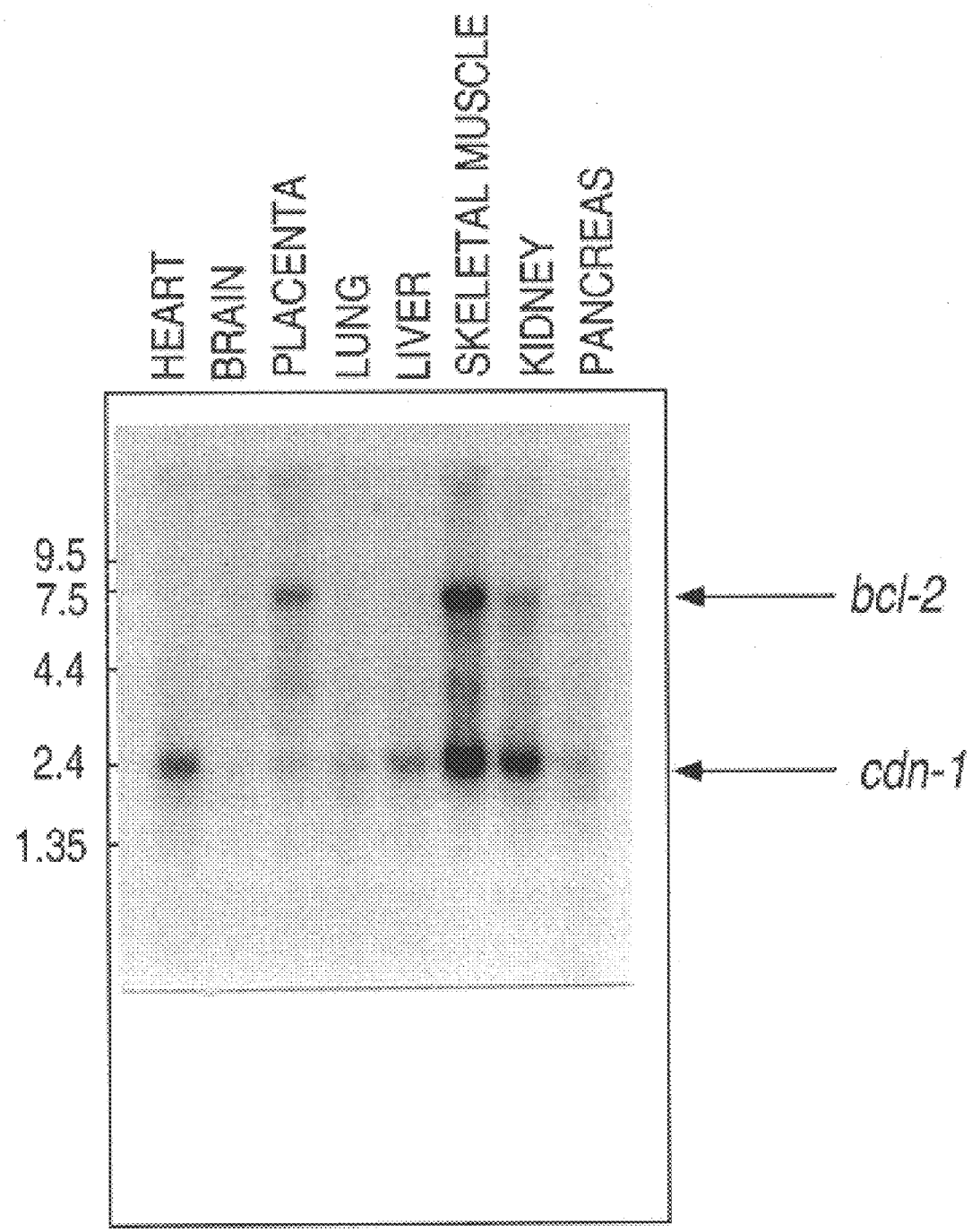
FIG. 4 depicts the results of a Northern blot analysis of multiple tissues with probes specific for both bcl-2 and cdn-1.

The results, presented in FIG. 4 indicate that cdn-1 is expressed in all organs tested (heart, brain, placenta, lung, liver, skeletal muscle, kidney and pancreas) whereas bcl-2 is not expressed or expressed at only low levels in heart, brain, lung, and liver. Thus, cdn-1 appears to be more widely expressed throughout human organs than bcl-2 and may be more important in regulating apoptosis in these tissues.

EXAMPLE 3

Expression of Recombinant cdn-1

In order to express recombinant cdn-1 in the baculovirus system, the cdn-1 cDNA generated in Example 1 was used to generate a novel cdn-1 vector, by a PCR methodology as described in Example 1, using primers from the 3' and 5' flanking regions of the gene which contain restriction sites to facilitate cloning. The plasmids were sequenced by the dideoxy terminator method (Sanger et al., 1977) using sequencing kits (USB, Sequenase version 2.0) and internal primers. This was to confirm that no mutations resulted from PCR.

A clone was used to generate recombinant viruses by in vivo homologous recombination between the overlapping sequences of the plasmid and AcNPV wild type baculovirus. After 48 hours post-transfection in insect Spodoptera frugiperda clone 9 (SF9) cells, the recombinant viruses were collected, identified by PCR and further purified. Standard procedures for selection, screening and propagation of recombinant baculovirus were performed (Invitrogen). The molecular mass, on sodium dodecyl sulfate-polyacrylamide gel electrophoresis (SDS-PAGE), of the protein produced in the baculovirus system was compared with the predicted molecular mass of cdn-1 according to the amino-acid sequence.

In addition, similar clones can be expressed preferably in a yeast intracellular expression system by any method known in the art, including the method described by Barr et al. (1992) Transgenesis ed. JAH Murray, (Wiley and Sons) pp. 55–79.

EXAMPLE 4

Expression of cdn-1 in Mammalian Systems

The cdn-1 coding sequence was excised from a plasmid generated in Example 1, and introduced into plasmids pCEP7, pREP7 and pcDNA3 (Invitrogen) at compatible restriction enzyme sites. pCEP7 was generated by removing the RSV 3'-LTR of pREP7 with XbaI/Asp718, and substituting the CMV promoter from pCEP4 (Invitrogen). 25 µg of each cdn-1-containing plasmid was electroporated into the B lymphoblastoid cell line WIL-2, and stable hygromycin resistant transformants or G418 resistant transformants (pcDNA3 constructs, FIG. 8) expressing cdn-1 were selected.

The coding region of cdns can also ligated into expression vectors capable of stably integrating into other cell types including but not limited to cardiomyocytes, neural cell lines such as GTI-7 and TNF sensitive cells such as the human colon adenocarcinoma cell line HT29 so as to provide a variety of assay systems to monitor the regulation of apoptosis by cdn-1.

EXAMPLE 5

Effect of the Anti-Apoptotic Activity of cdn-1 and its Derivatives in the Wild Type B Lymphoblastoid Cell Line WIL2-729 HF2 and the Transformed Cell Expressing Excess cdn-1

$2 \times 10^5$ WIL-2, and WIL-2 cells transformed with a vector encoding cdn-1 as described in Example 4 are grown in RPMI supplemented with 10% fetal bovine serum (FBS) for the anti-fas experiment or 0.1% FBS for serum deprivation experiments. In the case of the anti-fas experiment, after washing with fresh medium, the cells were suspended in RPMI supplemented with 10% FBS, exposed to anti-fas antibodies and the kinetics of cell death in response to an apoptosis inducing agent were analyzed by flow cytometry with FACScan. In the case of the serum deprivation experiment, the WIL-2 cells were resuspended in RPMI supplemented with 0.1% FBS and apoptosis was monitored according to the method described by Henderson et al. (1993) *Proc. Natl. Acad. Sci. USA* 90:8479–8483. Other methods of inducing apoptosis include, but are not limited to, oxygen deprivation in primary cardiac myocytes, NGF withdrawal, glutathione depletion in the neural cell line GTI-7 or TNF addition to the HT29 cell line. Apoptosis was assessed by measuring cell shrinkage and permeability to propidium iodide (PI) during their death. In addition, any other method of assessing apoptotic cell death may be used.

Figure 9:
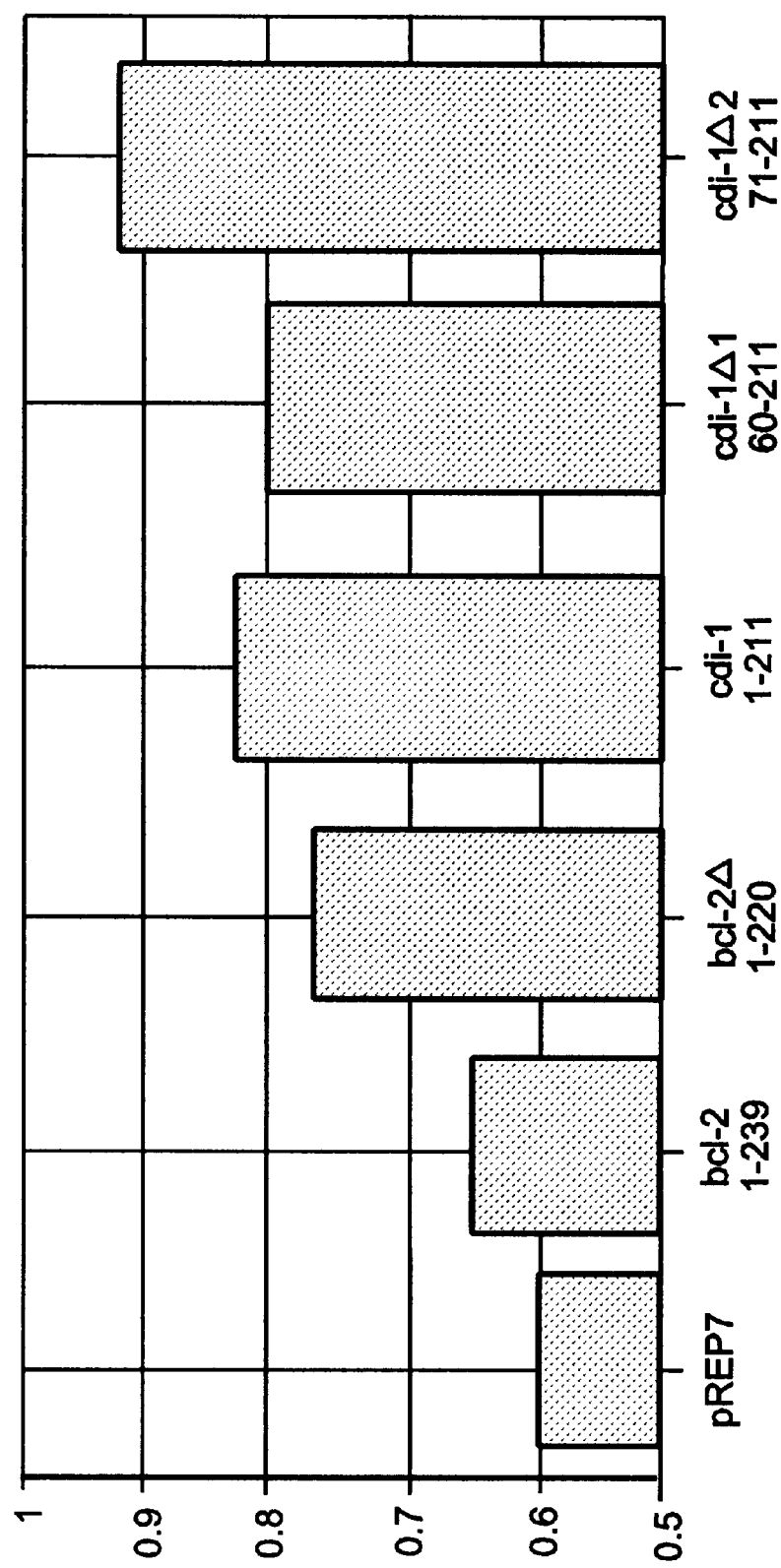
FIG. 9 shows anti-apoptotic effects of cdn-1 and some of its derivatives in FAS-induced apoptosis of WIL-2 cells.

FIG. 8 shows the anti-apoptotic response of various WIL-2 transformants to anti-Fas treatment. FIG. 9 shows the anti-apoptotic response of various WIL-2 transformants to serum deprivation. In FIG. 8, duplicate wells containing $3 \times 10^5$ cells were incubated with 50 ng/ml of the cytocidal anti-Fas antibody for 24 hours. Cell death was then analyzed by flow cytometry with FACScan. The proteins expressed from each construct are shown beneath the columns. Since many of the constructs are truncation or deletion variants, the exact amino acids expressed are also indicated. As can be seen, all of the transformants had some protective effect when compared to the control transformant containing the pREP7 vector alone. The most apoptosis-resistant transformant was the cdn-1Δ2 expressing cell line, in which over 90% of the cells survived anti-fas treatment. Significant protection was also observed in transformants expressing full length cdn-1 (1-211) and cdn-1Δ1, followed by bcl-2Δ and bcl-2 expressing cell lines.

Cdn-1Δ1 and cdn-1Δ2 are lacking the N-terminal 59 and 70 amino acids of the full length cdn-1 molecule, respectively. The observation that cdn-1Δ2 is more effective at blocking apoptosis than full length cdn-1 suggests that smaller, truncated cdn-1 molecules may be potent therapeutics.

EXAMPLE 6

Determination of other cdn genes and Cloning of the cdn-2 Gene

Southern blot analyses of human genome DNA and a panel of human/rodent somatic cell DNAs indicated that there were at least 3 cdn related genes and that they resided in chromosomes 6, 11 and 20. PCR/sequence analysis of the three hybrid DNAs showed that cdn-1 was on chromosome 6 and that two closely related sequences were on chromosome 20 (designated cdn-2) and chromosome 11 (designated cdn-3). We have cloned the cdn-2 and cdn-3 genes and sequenced them. Interestingly, both cdn-2 and cdn-3 do not contain introns and have all of the features of processed genes that have returned to the genome. cdn-3 has a nucleotide deletion, causing a frame shift and early termination and thus is probably a pseudogene. Both, however, have promoter elements upstream of the repeats CCAAT, TATAAA boxes but are probably not transcribed. (Northern blot analysis with cdn-2 and cdn-3 specified probes.)

900,000 clones from a human placenta genomic library in the cosmid vector pWE15 (Stratagene, La Jolla, Calif.) were screened with a 950 bp BglII- HindIII cDNA probe containing the entire coding region of Cdn-1. The probe was $^{32}$P-labeled according to the method of Feinberg and Vogelstein (1984) *Anal. Biochem.* 137:266–267. The library was processed and screened under high stringency hybridization and washing conditions as described by Sambrook et al. (1989) Molecular Cloning, 2nd edition, Cold Spring Harbor Laboratory Press. Ten double positive clones were further purified by replating and screening as above. Plasmid DNA was purified using the Wizard Maxiprep DNA Purification System as described by the supplier (Promega Corp., Madison, Wis.) and analyzed by EcoRI restriction enzyme mapping and Southern blotting. The probe used for Southern blotting and hybridization conditions was the same as above.

The cosmid clones fell into two groups as judged by EcoRI restriction analysis and Southern blotting. Cosmid clones (cos) 1–4 and 7 displayed one distinct pattern of EcoRI generated DNA fragments and contained a single 6.5 kb hybridizing EcoRI DNA fragment. Cos2 and Cos9 fell into the second group that was characterized by a 5.5 kb hybridizing EcoRI DNA fragment. The 6.5 kb DNA fragment from cos2 and the 5.5 kb DNA fragment from cos9 were subcloned into pBluescript SK⁻ (Stratagene, La Jolla, Calif.) using standard molecular biological techniques (Sambrook et al. as above). Plasmid DNA was isolated and the DNA inserts from two subclones, A4 (from cos2) and C5 (from cos9) were mapped with BamHI, HindIII and EcoRI and analyzed by Southern blotting as described above. Smaller restriction fragments from both clones were subcloned into M13 sequencing vectors and the DNA sequence was determined.

The sequence of A4 contains an open reading frame that displays 97% amino acid sequence identity with cdn-1. (FIG. 5) The high degree of sequence identity of this gene with cdn-1 indicates that it is a new cdn-1 related gene and therefore will be called cdn-2. A sequence comparison of the encoded cdn-2 protein and the other members of the bcl-2 family is shown in FIG. 5. Cdn-2 contains the conserved regions, BH1 and BH2, that are hallmarks of the bcl-2 family, and displays a lower overall sequence identity (~20–30%) to other members, which is also characteristic of the bcl-2 family. cdn-3 has a frame shift and therefore does not contain the structural features of cdn-1, cdn-2 or other bcl-2 family members.

EXAMPLE 7

Chromosomal Localization of the cdn-1 and cdn-2 Genes

Southern blot analysis of a panel of human/rodent somatic cell hybrid DNAs (Panel #2 DNA from the NIGMS, Camden, N.J.) and fluorescent in situ hybridization (FISH) of metaphase chromosomes were used to map the cdn genes to human chromosomes. For Southern blotting, 5 µg of hybrid panel DNA was digested with EcoRI or BamHI/HindIII, fractionated on 0.8% or 1% agarose gels, transferred to nitrocellulose and hybridized with the cdn-1 probe. Hybridization and washing conditions were as described above. For FISH, the cdn-2 subclone, A4, was biotinylated using the Bionick Labeling System (Gibco BRL, Gaithersburg, Md.) and hybridized to metaphase chromosomes from normal human fibroblasts according to the method described by viegas-Pequignot in In Situ Hybridization, A Practical Approach, 1992, ed. D. G. Wilkinson, pp. 137–158, IRL Press, Oxford. Probe detection using FITC-conjugated avidin and biotinylated goat anti-avidin was according to the method described by Pinkel et al. (1988) *Proc. Natl. Acad. Sci. USA* 85:9138–9142.

Southern blot analysis showed three hybridizing EcoRI bands in the human DNA control that were approximately 12 kb, 11 kb and 5.5 kb in length. Analysis of the somatic cell hybrid DNA indicated that the 12 kb band was in two different samples, NA10629, which contained only human chromosome 6, and NA07299, which contained both human chromosomes 1 and X and, importantly, a portion of chromosome 6 telomeric to p21. The 11 kb band was in NA13140, which contains human chromosome 20. The 5.5 kb hybridizing band was found only in sample NA10927A, which contained human chromosome 11. PCR/DNA sequencing analysis of these hybrid DNA samples using primers for cdn-1 or cdn-2, showed cdn-1 sequences in NA10629 (the chromosome 6-containing hybrid DNA) and NA07299 (the chromosome 1, X and 6pter>p21-containing hybrid DNA), indicating that the cdn-1 gene resides on chromosome 6, telomeric to p21. cdn-2 sequences were found in NA13140, indicating the cdn-2 gene resides on chromosome 20, and cdn-3 sequences were found in NA10927A, indicating the cdn-3 gene resides on chromosome 11.

EXAMPLE 8

Modulation of apoptosis by cdn-1 and cdn-2 in FL5.12 cells

FL5.12 is an IL-3-dependent lymphoid progenitor cell line (McKearn et al. (1985) *Proc. Natl. Acad. Sci USA* 82:7414–7418) that has been shown to undergo apoptosis following withdrawal of IL-3 but is protected from cell death by overexpression of bcl-2. Nunez et al. (1990) *J. Immunol.* 144:3602–3610; and Hockenbery et al. (1990) *Nature* 348:334–336. To assess the ability of cdn-1 and cdn-2 to modulate apoptosis, cDNAs encoding cdn-1, cdn-2, two truncated forms of cdn-1 (described below) and bcl-2 were ligated into the mammalian expression vector, pcDNA3 (Invitrogen, San Diego, Calif.) and stably introduced into the mouse progenitor B lymphocyte cell line FL5.12 by electroporation and selection in media containing the antibiotic G418. Assays were then performed on bulk transformants as described below.

The effects of the overexpressed genes on FL5.12 cell viability were examined at various times following withdrawal of IL-3 and are shown in FIG. 10. Cell viability was assessed by propidium iodide (PI) exclusion on a flow cytometer (Becton Dickinson FACScan). Bcl-2 expression protected the cells significantly from cell death while cdn-1 appeared to enhance cell death when compared to the vector control. Cdn-2 expression conferred a low level of protection from cell death at earlier times but was insignificant at later time points. Interestingly, cdn-1Δ2 gave a moderate level of protection against cell death. Cdn-1-112, a molecule that contains the N-terminal 112 amino acids of cdn-1, also appeared to partially protect the FL5.12 cells although at lower levels than Bcl-2.

As shown in Example 7, expression of cdn-1 and cdn-1Δ2 in WIL2 cells resulted in increased cell survival in response to anti-Fas-mediated apoptosis and serum withdrawal. Taken together, these data suggest that the various cdn molecules are capable of modulating apoptosis in a positive or negative manner, depending on the cell type and apoptotic stimuli. Thus, they are effective in preventing cell death such as in the post-ischemic reperfusion tissue damage in the heart or in inducing cell death in cells that have escaped apoptotic control, as is the case in various cancers.

Although the foregoing invention has been described in some detail by way of illustration and example for purposes of clarity of understanding, it will be apparent to those skilled in the art that certain changes and modifications may be practiced. Therefore, the description and examples should not be construed as limiting the scope of the invention, which is delineated by the appended claims.

---

We claim:

1. A method of modulating the level of an apoptosis-modulating protein in a cell in vitro, comprising the steps of:
providing a cell in vitro; and
introducing into the cell a polynucleotide encoding a CDN protein, wherein the CDN protein is a homologue of bcl-2 and is selected from the group consisting of a CDN-1 comprising the amino acid sequence of SEQ ID NO: 7, and a CDN-2 comprising the amino acid sequence of SEQ ID NO: 9; and wherein said polynucleotide encoding a CDN protein is expressed at a level sufficient to modulate apoptosis in the cell.

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 8 amino acids
      (B) TYPE: amino acid
      (C) STRANDEDNESS: single (D) TOPOLOGY: linear (xi) SEQUENCE DESCRIPTION: SEQ ID NO:1:

Asp Trp Gly Arg Val Val Ala Ile
1               5

(2) INFORMATION FOR SEQ ID NO:2:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ix) FEATURE:
        (A) NAME/KEY: misc_difference
        (B) LOCATION: replace(23, "")
        (D) OTHER INFORMATION: /note= "This position is inosine."

(ix) FEATURE:
        (A) NAME/KEY: misc_difference
        (B) LOCATION: replace(27, "")
        (D) OTHER INFORMATION: /note= "This position is inosine."

(xi) SEQUENCE DESCRIPTION: SEQ ID NO:2:

AGATCTGAAT TCAACTTGGG GGNCAGNAGT NGTNGC                      36

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:3:

Asp Trp Gly Gly Gln Glu Asn Asp Gln Ile Trp
1               5                   10

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ix) FEATURE:
        (A) NAME/KEY: misc_difference
        (B) LOCATION: replace(6, "")
        (D) OTHER INFORMATION: /note= "This position is inosine."

(ix) FEATURE:
        (A) NAME/KEY: misc_difference
        (B) LOCATION: replace(9, "")
        (D) OTHER INFORMATION: /note= "This position is inosine."

(xi) SEQUENCE DESCRIPTION: SEQ ID NO:4:

AGGGTNGGNG GNACNAGAGA CATCTAGGT                              29

(2) INFORMATION FOR SEQ ID NO:5:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ix) FEATURE:
        (A) NAME/KEY: misc_difference
        (B) LOCATION: replace(19, "")
        (D) OTHER INFORMATION: /note= "This position is inosine."

(ix) FEATURE:
      (A) NAME/KEY: misc_difference
      (B) LOCATION: replace(22, "")
      (D) OTHER INFORMATION: /note= "This position is inosine."

(xi) SEQUENCE DESCRIPTION: SEQ ID NO:5:

AGATCTAAGC TTGTCCCANC CNCCNTGNTC CTTGAGATCC A                         41

(2) INFORMATION FOR SEQ ID NO:6:

(i) SEQUENCE CHARACTERISTICS:
      (A) LENGTH: 2094 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 201..833

(xi) SEQUENCE DESCRIPTION: SEQ ID NO:6:

GAGGATCTAC AGGGGACAAG TAAAGGCTAC ATCCAGATGC CGGGAATGCA CTGACGCCCA      60

TTCCTGGAAA CTGGGCTCCC ACTCAGCCCC TGGGAGCAGC AGCCGCCAGC CCCTCGGACC    120

TCCATCTCCA CCCTGCTGAG CCACCCGGGT TGGGCCAGGA TCCCGGCAGG CTGATCCCGT    180

CCTCCACTGA GACCTGAAAA ATG GCT TCG GGG CAA GGC CCA GGT CCT CCC        230
                      Met Ala Ser Gly Gln Gly Pro Gly Pro Pro
                       1               5                  10

AGG CAG GAG TGC GGA GAG CCT GCC CTG CCC TCT GCT TCT GAG GAG CAG      278
Arg Gln Glu Cys Gly Glu Pro Ala Leu Pro Ser Ala Ser Glu Glu Gln
                15                  20                  25

GTA GCC CAG GAC ACA GAG GAG GTT TTC CGC AGC TAC GTT TTT TAC CGC      326
Val Ala Gln Asp Thr Glu Glu Val Phe Arg Ser Tyr Val Phe Tyr Arg
            30                  35                  40

CAT CAG CAG GAA CAG GAG GCT GAA GGG GTG GCT GCC CCT GCC GAC CCA      374
His Gln Gln Glu Gln Glu Ala Glu Gly Val Ala Ala Pro Ala Asp Pro
        45                  50                  55

GAG ATG GTC ACC TTA CCT CTG CAA CCT AGC AGC ACC ATG GGG CAG GTG      422
Glu Met Val Thr Leu Pro Leu Gln Pro Ser Ser Thr Met Gly Gln Val
    60                  65                  70

GGA CGG CAG CTC GCC ATC ATC GGG GAC GAC ATC AAC CGA CGC TAT GAC      470
Gly Arg Gln Leu Ala Ile Ile Gly Asp Asp Ile Asn Arg Arg Tyr Asp
75                  80                  85                  90

TCA GAG TTC CAG ACC ATG TTG CAG CAC CTG CAG CCC ACG GCA GAG AAT      518
Ser Glu Phe Gln Thr Met Leu Gln His Leu Gln Pro Thr Ala Glu Asn
                95                 100                 105

GCC TAT GAG TAC TTC ACC AAG ATT GCC ACC AGC CTG TTT GAG AGT GGC      566
Ala Tyr Glu Tyr Phe Thr Lys Ile Ala Thr Ser Leu Phe Glu Ser Gly
            110                 115                 120

ATC AAT TGG GGC CGT GTG GTG GCT CTT CTG GGC TTC GGC TAC CGT CTG      614
Ile Asn Trp Gly Arg Val Val Ala Leu Leu Gly Phe Gly Tyr Arg Leu
        125                 130                 135

GCC CTA CAC GTC TAC CAG CAT GGC CTG ACT GGC TTC CTA GGC CAG GTG      662
Ala Leu His Val Tyr Gln His Gly Leu Thr Gly Phe Leu Gly Gln Val
    140                 145                 150

ACC CGC TTC GTG GTC GAC TTC ATG CTG CAT CAC TGC ATT GCC CGG TGG      710
Thr Arg Phe Val Val Asp Phe Met Leu His His Cys Ile Ala Arg Trp
155                 160                 165                 170

ATT GCA CAG AGG GGT GGC TGG GTG GCA GCC CTG AAC TTG GGC AAT GGT      758
Ile Ala Gln Arg Gly Gly Trp Val Ala Ala Leu Asn Leu Gly Asn Gly
                175                 180                 185

CCC ATC CTG AAC GTG CTG GTG GTT CTG GGT GTG GTT CTG TTG GGC CAG      806

```
        Pro Ile Leu Asn Val Leu Val Val Leu Gly Val Val Leu Leu Gly Gln
                    190                 195                 200

TTT GTG GTA CGA AGA TTC TTC AAA TCA TGACTCCCAA GGGTGCCCTT           853
Phe Val Val Arg Arg Phe Phe Lys Ser
            205                 210

TGGGTCCCGG TTCAGACCCC TGCCTGGACT TAAGCGAAGT CTTTGCCTTC TCTGTTCCCT   913

TGCAGGGTCC CCCCTCAAGA GTACAGAAGC TTTAGCAAGT GTGCACTCCA GCTTCGGAGG   973

CCCTGCGTGG GGGCCAGTCA GGCTGCAGAG GCACCTCAAC ATTGCATGGT GCTAGTGCCC  1033

TCTCTCTGGG CCCAGGGCTG TGGCCGTCTC CTCCCTCAGC TCTCTGGGAC CTCCTTAGCC  1093

CTGTCTGCTA GGCGCTGGGG AGACTGATAA CTTGGGGAGG CAAGAGACTG GGAGCCACTT  1153

CTCCCCAGAA AGTGTTTAAC GGTTTTAGCT TTTTATAATA CCCTTGTGAG AGCCCATTCC  1213

CACCATTCTA CCTGAGGCCA GGACGTCTGG GGTGTGGGGA TTGGTGGGTC TATGTTCCCC  1273

AGGATTCAGC TATTCTGGAA GATCAGCACC CTAAGAGATG GGACTAGGAC CTGAGCCTGG  1333

TCCTGGCCGT CCCTAAGCAT GTGTCCCAGG AGCAGGACCT ACTAGGAGAG GGGGGCCAAG  1393

GTCCTGCTCA ACTCTACCCC TGCTCCCATT CCTCCCTCCG GCCATACTGC CTTTGCAGTT  1453

GGACTCTCAG GGATTCTGGG CTTGGGGTGT GGGGTGGGGT GGAGTCGCAG ACCAGAGCTG  1513

TCTGAACTCA CGTGTCAGAA GCCTCCAAGC CTGCCTCCCA AGGTCCTCTC AGTTCTCTCC  1573

CTTCCTCTCT CCTTATAGAC ACTTGCTCCC AACCCATTCA CTACAGGTGA AGGCTCTCAC  1633

CCATCCCTGG GGGCCTTGGG TGAGTGGCCT GCTAAGGCTC CTCCTTGCCC AGACTACAGG  1693

GCTTAGGACT TGGTTTGTTA TATCAGGGAA AAGGAGTAGG GAGTTCATCT GGAGGGTTCT  1753

AAGTGGGAGA AGGACTATCA ACACCACTAG GAATCCCAGA GGTGGATCCT CCCTCATGGC  1813

TCTGGCACAG TGTAATCCAG GGGTGTAGAT GGGGGAACTG TGAATACTTG AACTCTGTTC  1873

CCCCACCCTC CATGCTCCTC ACCTGTCTAG GTCTCCTCAG GGTGGGGGGT GACAGTGCCT  1933

TCTCTATTGG CACAGCCTAG GGTCTTGGGG GTCAGGGGGG AGAAGTTCTT GATTCAGCCA  1993

AATGCAGGGA GGGGAGGCAG ATGGAGCCCA TAGGCCACCC CCTATCCTCT GAGTGTTTGG  2053

AAATAAACTG TGCAATCCCC TCAAAAAAAA AACGGAGATC C                      2094

(2) INFORMATION FOR SEQ ID NO:7:

(i) SEQUENCE CHARACTERISTICS:
        (A) LENGTH: 211 amino acids
        (B) TYPE: amino acid
        (D) TOPOLOGY: linear (ii) MOLECULE TYPE: protein (xi) SEQUENCE DESCRIPTION: SEQ ID NO:7:

Met Ala Ser Gly Gln Gly Pro Gly Pro Pro Arg Gln Glu Cys Gly Glu
  1               5                  10                  15

Pro Ala Leu Pro Ser Ala Ser Glu Glu Gln Val Ala Gln Asp Thr Glu
             20                  25                  30

Glu Val Phe Arg Ser Tyr Val Phe Tyr Arg His Gln Gln Glu Gln Glu
         35                  40                  45

Ala Glu Gly Val Ala Ala Pro Ala Asp Pro Glu Met Val Thr Leu Pro
     50                  55                  60

Leu Gln Pro Ser Ser Thr Met Gly Gln Val Gly Arg Gln Leu Ala Ile
 65                  70                  75                  80

Ile Gly Asp Asp Ile Asn Arg Arg Tyr Asp Ser Glu Phe Gln Thr Met
                 85                  90                  95

Leu Gln His Leu Gln Pro Thr Ala Glu Asn Ala Tyr Glu Tyr Phe Thr
```

```
                 100                 105                 110
Lys Ile Ala Thr Ser Leu Phe Glu Ser Gly Ile Asn Trp Gly Arg Val
        115                 120                 125
Val Ala Leu Leu Gly Phe Gly Tyr Arg Leu Ala Leu His Val Tyr Gln
130                 135                 140
His Gly Leu Thr Gly Phe Leu Gly Gln Val Thr Arg Phe Val Val Asp
145                 150                 155                 160
Phe Met Leu His His Cys Ile Ala Arg Trp Ile Ala Gln Arg Gly Gly
                165                 170                 175
Trp Val Ala Ala Leu Asn Leu Gly Asn Gly Pro Ile Leu Asn Val Leu
            180                 185                 190
Val Val Leu Gly Val Val Leu Leu Gly Gln Phe Val Val Arg Arg Phe
        195                 200                 205
Phe Lys Ser
    210

(2) INFORMATION FOR SEQ ID NO:8:

(i) SEQUENCE CHARACTERISTICS:
        (A) LENGTH: 1287 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 544..1176

(xi) SEQUENCE DESCRIPTION: SEQ ID NO:8:

TTTTAATATA AATTAATGTG CTCTATTTAT AGAGACAATA CATGAAATAT ACTTAATAAA      60

AATTCAAATG TTATAGAACT GAAAAGATG  AAAAGTAAAA ACAACCTATT CCCCAGAGGT     120

AGCCACTGTC CATAGTTTCT ATTTTAGATT CTTTCCTTTA TACAAGATTA TTATAGCTTC    180

TATTTTTTGG TGTATGAACT GTAGTCCTAG AGGATTTTAT TAGTTATGAG TTCTATAACT    240

AAGATCCATC ATCTTAGTTG CTAAGAACGT AGATACTGAG AACATCATTT AAAAAAACAT    300

TTTTGGCTGG CACCTCATGA TCACTGGAGT CTCGCGGGTC CCTCAGGCTG CACAGGGACA    360

AGTAAAGGCT ACATCCAGAT GCTGGGAATG CACTGACGCC CATTCCTGGA AACTGGGCTC    420

CCACTCAGCC CCTGGGAGCA GCAGCCGCCA GCCCCTCGGG ACCTCCATCT CCACCCTGCT    480

GAGCCACCCG GGTTGGGCCA GGATCCCGGC AGGCTGATCC CGTCCTCCAC TGAGACCTGA    540

AAA ATG GCT TCG GGG CAA GGC CCA GGT CCT CCC AGG CAG GAG TGC GGA       588
    Met Ala Ser Gly Gln Gly Pro Gly Pro Pro Arg Gln Glu Cys Gly
        215                 220                 225

GAG CCT GCC CTG CCC TCT GCT TCT GAG GAG CAG GTA GCC CAG GAC ACA       636
Glu Pro Ala Leu Pro Ser Ala Ser Glu Glu Gln Val Ala Gln Asp Thr
                230                 235                 240

GAG GAG GTT TTC CGC AGC TAC GTT TTT TAC CAC CAT CAG CAG GAA CAG       684
Glu Glu Val Phe Arg Ser Tyr Val Phe Tyr His His Gln Gln Glu Gln
            245                 250                 255

GAG GCT GAA GGG GCG GCT GCC CCT GCC GAC CCA GAG ATG GTC ACC TTA       732
Glu Ala Glu Gly Ala Ala Ala Pro Ala Asp Pro Glu Met Val Thr Leu
        260                 265                 270

CCT CTG CAA CCT AGC AGC ACC ATG GGG CAG GTG GGA CGG CAG CTC GCC       780
Pro Leu Gln Pro Ser Ser Thr Met Gly Gln Val Gly Arg Gln Leu Ala
275                 280                 285                 290

ATC ATT GGG GAC GAC ATC AAC CGA CGC TAT GAC TCA GAG TTC CAG ACC       828
Ile Ile Gly Asp Asp Ile Asn Arg Arg Tyr Asp Ser Glu Phe Gln Thr
                295                 300                 305
```

```
ATG TTG CAG CAC CTG CAG CCC ACG GCA GAG AAT GCC TAT GAG TAC TTC    876
Met Leu Gln His Leu Gln Pro Thr Ala Glu Asn Ala Tyr Glu Tyr Phe
        310                 315                 320

ACC AAG ATT GCC TCC AGC CTG TTT GAG AGT GGC ATC AAT TGG GGC CGT    924
Thr Lys Ile Ala Ser Ser Leu Phe Glu Ser Gly Ile Asn Trp Gly Arg
            325                 330                 335

GTG GTG GCT CTT CTG GGC TTC AGC TAC CGT CTG GCC CTA CAC ATC TAC    972
Val Val Ala Leu Leu Gly Phe Ser Tyr Arg Leu Ala Leu His Ile Tyr
    340                 345                 350

CAG CGT GGC CTG ACT GGC TTC CTG GGC CAG GTG ACC CGC TTT GTG GTG   1020
Gln Arg Gly Leu Thr Gly Phe Leu Gly Gln Val Thr Arg Phe Val Val
355                 360                 365                 370

GAC TTC ATG CTG CAT CAC TGC ATT GCC CGG TGG ATT GCA CAG AGG GGT   1068
Asp Phe Met Leu His His Cys Ile Ala Arg Trp Ile Ala Gln Arg Gly
                375                 380                 385

GGC TGG GTG GCA GCC CTG AAC TTG GGC AAT GGT CCC ATC CTG AAC GTG   1116
Gly Trp Val Ala Ala Leu Asn Leu Gly Asn Gly Pro Ile Leu Asn Val
            390                 395                 400

CTG GTG GTT CTG GGT GTG GTT CTG TTG GGC CAG TTT GTG GTA CGA AGA   1164
Leu Val Val Leu Gly Val Val Leu Leu Gly Gln Phe Val Val Arg Arg
    405                 410                 415

TTC TTC AAA TCA TGACTCCCAA GGGTGCCTTT GGGGTCCCAG TTCAGACCCC       1216
Phe Phe Lys Ser
        420

TGCCTGGACT TAAGCGAAGT CTTTGCCTTC TCTGCTCCTT GCAGGGTCCC CCCTCAAGAG 1276

TACAGAAGCT T                                                      1287

(2) INFORMATION FOR SEQ ID NO:9:

(i) SEQUENCE CHARACTERISTICS:
        (A) LENGTH: 211 amino acids
        (B) TYPE: amino acid
        (D) TOPOLOGY: linear (ii) MOLECULE TYPE: protein (xi) SEQUENCE DESCRIPTION: SEQ ID NO:9:

Met Ala Ser Gly Gln Gly Pro Gly Pro Pro Arg Gln Glu Cys Gly Glu
  1               5                  10                  15

Pro Ala Leu Pro Ser Ala Ser Glu Glu Gln Val Ala Gln Asp Thr Glu
                 20                  25                  30

Glu Val Phe Arg Ser Tyr Val Phe Tyr His His Gln Gln Glu Gln Glu
             35                  40                  45

Ala Glu Gly Ala Ala Ala Pro Ala Asp Pro Glu Met Val Thr Leu Pro
         50                  55                  60

Leu Gln Pro Ser Ser Thr Met Gly Gln Val Gly Arg Gln Leu Ala Ile
 65                  70                  75                  80

Ile Gly Asp Asp Ile Asn Arg Arg Tyr Asp Ser Glu Phe Gln Thr Met
                 85                  90                  95

Leu Gln His Leu Gln Pro Thr Ala Glu Asn Ala Tyr Glu Tyr Phe Thr
            100                 105                 110

Lys Ile Ala Ser Ser Leu Phe Glu Ser Gly Ile Asn Trp Gly Arg Val
        115                 120                 125

Val Ala Leu Leu Gly Phe Ser Tyr Arg Leu Ala Leu His Ile Tyr Gln
    130                 135                 140

Arg Gly Leu Thr Gly Phe Leu Gly Gln Val Thr Arg Phe Val Val Asp
145                 150                 155                 160

Phe Met Leu His His Cys Ile Ala Arg Trp Ile Ala Gln Arg Gly Gly
                165                 170                 175
```

```
Trp Val Ala Ala Leu Asn Leu Gly Asn Gly Pro Ile Leu Asn Val Leu
            180                 185                 190

Val Val Leu Gly Val Val Leu Leu Gly Gln Phe Val Val Arg Arg Phe
            195                 200                 205

Phe Lys Ser
    210

(2) INFORMATION FOR SEQ ID NO:10:

(i) SEQUENCE CHARACTERISTICS:
        (A) LENGTH: 211 amino acids
        (B) TYPE: amino acid
        (C) STRANDEDNESS: single
        (D) TOPOLOGY: linear (xi) SEQUENCE DESCRIPTION: SEQ ID NO:10:

Met Ala Ser Gly Gln Gly Pro Gly Pro Pro Arg Gln Glu Cys Gly Glu
1               5                   10                  15

Pro Ala Leu Pro Ser Ala Ser Glu Glu Gln Val Ala Gln Asp Thr Glu
            20                  25                  30

Glu Val Phe Arg Ser Tyr Val Phe Tyr Arg His Gln Gln Glu Gln Glu
            35                  40                  45

Ala Glu Gly Val Ala Ala Pro Ala Asp Pro Glu Met Val Thr Leu Pro
50                      55                  60

Leu Gln Pro Ser Ser Thr Met Gly Gln Val Gly Arg Gln Leu Ala Ile
65                  70                  75                  80

Ile Gly Asp Asp Ile Asn Arg Arg Tyr Asp Ser Glu Phe Gln Thr Met
                85                  90                  95

Leu Gln His Leu Gln Pro Thr Ala Glu Asn Ala Tyr Glu Tyr Phe Thr
            100                 105                 110

Lys Ile Ala Thr Ser Leu Phe Glu Ser Gly Ile Asn Trp Gly Arg Val
            115                 120                 125

Val Ala Leu Leu Gly Phe Gly Tyr Arg Leu Ala Leu His Val Tyr Gln
            130                 135                 140

His Gly Leu Thr Gly Phe Leu Gly Gln Val Thr Arg Phe Val Val Asp
145                 150                 155                 160

Phe Met Leu His His Cys Ile Ala Arg Trp Ile Ala Gln Arg Gly Gly
                165                 170                 175

Trp Val Ala Ala Leu Asn Leu Gly Asn Gly Pro Ile Leu Asn Val Leu
            180                 185                 190

Val Val Leu Gly Val Val Leu Leu Gly Gln Phe Val Val Arg Arg Phe
            195                 200                 205

Phe Lys Ser
    210

(2) INFORMATION FOR SEQ ID NO:11:

(i) SEQUENCE CHARACTERISTICS:
        (A) LENGTH: 211 amino acids
        (B) TYPE: amino acid
        (C) STRANDEDNESS: single
        (D) TOPOLOGY: linear (xi) SEQUENCE DESCRIPTION: SEQ ID NO:11:

Met Ala Ser Gly Gln Gly Pro Gly Pro Pro Arg Gln Glu Cys Gly Glu
1               5                   10                  15

Pro Ala Leu Pro Ser Ala Ser Glu Glu Gln Val Ala Gln Asp Thr Glu
            20                  25                  30
```

```
Glu Val Phe Arg Ser Tyr Val Phe Tyr His His Gln Gln Glu Gln Glu
         35                  40                  45

Ala Glu Gly Ala Ala Pro Ala Asp Pro Glu Met Val Thr Leu Pro
    50                  55                  60

Leu Gln Pro Ser Ser Thr Met Gly Gln Val Gly Arg Gln Leu Ala Ile
65                   70                  75                   80

Ile Gly Asp Asp Ile Asn Arg Arg Tyr Asp Ser Glu Phe Gln Thr Met
                 85                  90                  95

Leu Gln His Leu Gln Pro Thr Ala Glu Asn Ala Tyr Glu Tyr Phe Thr
            100                 105                 110

Lys Ile Ala Ser Ser Leu Phe Glu Ser Gly Ile Asn Trp Gly Arg Val
            115                 120                 125

Val Ala Leu Leu Gly Phe Ser Tyr Arg Leu Ala Leu His Ile Tyr Gln
            130                 135                 140

Arg Gly Leu Thr Gly Phe Leu Gly Gln Val Thr Arg Phe Val Val Asp
145                 150                 155                 160

Phe Met Leu His His Cys Ile Ala Arg Trp Ile Ala Gln Arg Gly Gly
                165                 170                 175

Trp Val Ala Ala Leu Asn Leu Gly Asn Gly Pro Ile Leu Asn Val Leu
                180                 185                 190

Val Val Leu Gly Val Val Leu Leu Gly Gln Phe Val Val Arg Arg Phe
            195                 200                 205

Phe Lys Ser
    210

(2) INFORMATION FOR SEQ ID NO:12:

(i) SEQUENCE CHARACTERISTICS:
        (A) LENGTH: 239 amino acids
        (B) TYPE: amino acid
        (C) STRANDEDNESS: single
        (D) TOPOLOGY: linear (xi) SEQUENCE DESCRIPTION: SEQ ID NO:12:

Met Ala His Ala Gly Arg Thr Gly Tyr Asp Asn Arg Glu Ile Val Met
1                5                  10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
            35                  40                  45

Phe Ser Ser Gln Pro Gly His Thr Pro His Thr Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
            85                  90                  95

Leu Arg Gln Ala Gly Asp Asp Phe Ser Arg Arg Tyr Arg Arg Asp Phe
            100                 105                 110

Ala Glu Met Ser Arg Gln Leu His Leu Thr Pro Phe Thr Ala Arg Gly
            115                 120                 125

Arg Phe Ala Thr Val Val Glu Glu Leu Phe Arg Asp Gly Val Asn Trp
            130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175
```

```
Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
210                 215                 220

Leu Val Gly Ala Cys Ile Thr Leu Gly Ala Tyr Leu Gly His Lys
225                 230                 235
```

(2) INFORMATION FOR SEQ ID NO:13:

(i) SEQUENCE CHARACTERISTICS:
        (A) LENGTH: 192 amino acids
        (B) TYPE: amino acid
        (C) STRANDEDNESS: single
        (D) TOPOLOGY: linear (xi) SEQUENCE DESCRIPTION: SEQ ID NO:13:

```
Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
            35                  40                  45

Pro Val Pro Gln Asp Ala Ser Thr Lys Lys Leu Ser Glu Cys Leu Lys
50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
            115                 120                 125

Val Pro Glu Leu Ile Arg Thr Ile Met Gly Trp Thr Leu Asp Phe Leu
            130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190
```

(2) INFORMATION FOR SEQ ID NO:14:

(i) SEQUENCE CHARACTERISTICS:
        (A) LENGTH: 233 amino acids
        (B) TYPE: amino acid
        (C) STRANDEDNESS: single
        (D) TOPOLOGY: linear (xi) SEQUENCE DESCRIPTION: SEQ ID NO:14:

```
Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
            35                  40                  45

Ser Ala Ile Asn Gly Asn Pro Ser Trp His Leu Ala Asp Ser Pro Ala
```

```
                    50                  55                  60
Val Asn Gly Ala Thr Gly His Ser Ser Ser Leu Asp Ala Arg Glu Val
 65                  70                  75                  80

Ile Pro Met Ala Ala Val Lys Gln Ala Leu Arg Glu Ala Gly Asp Glu
                     85                  90                  95

Phe Glu Leu Arg Tyr Arg Arg Ala Phe Ser Asp Leu Thr Ser Gln Leu
                    100                 105                 110

His Ile Thr Pro Gly Thr Ala Tyr Gln Ser Phe Glu Gln Val Val Asn
                    115                 120                 125

Glu Leu Phe Arg Asp Gly Val Asn Trp Gly Arg Ile Val Ala Phe Phe
                    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                    165                 170                 175

His Leu Glu Pro Trp Ile Gln Glu Asn Gly Gly Trp Asp Thr Phe Val
                    180                 185                 190

Glu Leu Tyr Gly Asn Asn Ala Ala Ala Glu Ser Arg Lys Gly Gln Glu
                    195                 200                 205

Arg Phe Asn Arg Trp Phe Leu Thr Gly Met Thr Val Ala Gly Val Val
                    210                 215                 220

Leu Leu Gly Ser Leu Phe Ser Arg Lys
225                 230
```

(2) INFORMATION FOR SEQ ID NO:15:

(i) SEQUENCE CHARACTERISTICS:
        (A) LENGTH: 226 amino acids
        (B) TYPE: amino acid
        (C) STRANDEDNESS: single
        (D) TOPOLOGY: linear (xi) SEQUENCE DESCRIPTION: SEQ ID NO:15:

```
Glu Leu Asp Gly Tyr Glu Pro Glu Pro Leu Gly Lys Arg Pro Ala Val
 1                   5                  10                  15

Leu Pro Leu Leu Glu Leu Val Gly Glu Ser Gly Asn Asn Thr Ser Thr
                     20                  25                  30

Asp Gly Ser Leu Pro Ser Thr Pro Pro Ala Glu Glu Glu Glu Glu Asp
                     35                  40                  45

Glu Leu Tyr Arg Gln Ser Leu Glu Ile Ile Ser Arg Tyr Leu Arg Glu
                     50                  55                  60

Gln Ala Thr Gly Ala Lys Asp Thr Lys Pro Met Gly Arg Ser Gly Ala
 65                  70                  75                  80

Thr Ser Arg Lys Ala Leu Glu Thr Leu Arg Arg Val Gly Asp Gly Val
                     85                  90                  95

Gln Arg Asn His Glu Thr Val Phe Gln Gly Met Leu Arg Lys Leu Asp
                    100                 105                 110

Ile Lys Asn Glu Asp Asp Val Lys Ser Leu Ser Arg Val Met Ile His
                    115                 120                 125

Val Phe Ser Asp Gly Val Thr Asn Trp Gly Arg Ile Val Thr Leu Ile
                    130                 135                 140

Ser Phe Gly Ala Phe Val Ala Lys His Leu Lys Thr Ile Asn Gln Glu
145                 150                 155                 160

Ser Cys Ile Glu Pro Leu Ala Glu Ser Ile Thr Asp Val Leu Val Arg
                    165                 170                 175

Thr Lys Arg Asp Trp Leu Val Lys Gln Arg Gly Trp Asp Gly Phe Val
```

```
                    180               185                190
Glu Phe Phe His Val Glu Asp Leu Glu Gly Gly Ile Arg Asn Val Leu
            195                 200                205

Leu Ala Phe Ala Gly Val Ala Gly Val Gly Ala Gly Leu Ala Tyr Leu
    210                 215                 220

Ile Arg
225

(2) INFORMATION FOR SEQ ID NO:16:

(i) SEQUENCE CHARACTERISTICS:
        (A) LENGTH: 172 amino acids
        (B) TYPE: amino acid
        (C) STRANDEDNESS: single
        (D) TOPOLOGY: linear (xi) SEQUENCE DESCRIPTION: SEQ ID NO:16:

Met Ala Glu Ser Glu Leu Met His Ile His Ser Leu Ala Glu His Tyr
1               5                   10                  15

Leu Gln Tyr Val Leu Gln Val Pro Ala Phe Glu Ser Ala Pro Ser Gln
            20                  25                  30

Ala Cys Arg Val Leu Gln Arg Val Ala Phe Ser Val Gln Lys Glu Val
        35                  40                  45

Glu Lys Asn Leu Lys Ser Tyr Leu Asp Asp Phe His Val Glu Ser Ile
    50                  55                  60

Asp Thr Ala Arg Ile Ile Phe Asn Gln Val Met Glu Lys Glu Phe Glu
65                  70                  75                  80

Asp Gly Ile Ile Asn Trp Gly Arg Ile Val Thr Ile Phe Ala Phe Gly
                85                  90                  95

Gly Val Leu Leu Lys Lys Leu Pro Gln Glu Gln Ile Ala Leu Asp Val
            100                 105                 110

Cys Ala Tyr Lys Gln Val Ser Ser Phe Val Ala Glu Phe Ile Met Asn
        115                 120                 125

Asn Thr Gly Glu Trp Ile Arg Gln Asn Gly Gly Trp Glu Asp Gly Phe
    130                 135                 140

Ile Lys Lys Phe Glu Pro Lys Ser Gly Trp Leu Thr Phe Leu Gln Met
145                 150                 155                 160

Thr Gly Gln Ile Trp Glu Met Leu Phe Leu Leu Lys
                165                 170

(2) INFORMATION FOR SEQ ID NO:17:

(i) SEQUENCE CHARACTERISTICS:
        (A) LENGTH: 187 amino acids
        (B) TYPE: amino acid
        (C) STRANDEDNESS: single
        (D) TOPOLOGY: linear (xi) SEQUENCE DESCRIPTION: SEQ ID NO:17:

Met Ala Tyr Ser Thr Arg Glu Ile Leu Leu Ala Leu Cys Ile Arg Asp
1               5                   10                  15

Ser Arg Val His Gly Asn Gly Thr Leu His Pro Val Leu Glu Leu Ala
            20                  25                  30

Ala Arg Glu Thr Pro Leu Arg Leu Ser Pro Glu Asp Thr Val Val Leu
        35                  40                  45

Arg Tyr His Val Leu Leu Glu Glu Ile Ile Glu Arg Asn Ser Glu Thr
    50                  55                  60

Phe Thr Glu Thr Trp Asn Arg Phe Ile Thr His Thr Glu His Val Asp
65                  70                  75                  80
```

```
Leu Asp Phe Asn Ser Val Phe Leu Glu Ile Phe His Asp Leu Ile Asn
                85                  90                  95

Trp Gly Arg Ile Cys Gly Phe Ile Val Phe Ser Ala Arg Met Ala Lys
               100                 105                 110

Tyr Cys Lys Asp Ala Asn Asn His Leu Glu Ser Thr Val Ile Thr Thr
               115                 120                 125

Ala Tyr Asn Phe Ser Glu Gly Leu Asp Gly Trp Ile His Gln Gln Gly
               130                 135                 140

Gly Trp Ser Thr Leu Ile Glu Asp Asn Ile Pro Gly Ser Arg Arg Phe
145                 150                 155                 160

Ser Trp Thr Leu Phe Leu Ala Gly Leu Thr Leu Ser Leu Leu Val Ile
               165                 170                 175

Cys Ser Tyr Leu Phe Ile Ser Arg Gly Arg His
               180                 185
```

(2) INFORMATION FOR SEQ ID NO:18:

(i) SEQUENCE CHARACTERISTICS:
        (A) LENGTH: 181 amino acids
        (B) TYPE: amino acid
        (C) STRANDEDNESS: single
        (D) TOPOLOGY: linear (xi) SEQUENCE DESCRIPTION: SEQ ID NO:18:

```
Met Glu Gly Glu Glu Leu Ile Tyr His Asn Ile Ile Asn Glu Ile Leu
1               5                   10                  15

Val Gly Tyr Ile Lys Tyr Tyr Met Asn Asp Ile His Glu Leu Ser Pro
                20                  25                  30

Tyr Gln Gln Gln Ile Lys Lys Ile Leu Thr Tyr Tyr Asp Glu Cys Leu
                35                  40                  45

Asn Lys Gln Val Thr Ile Thr Phe Ser Leu Thr Asn Ala Gln Glu Ile
50                  55                  60

Lys Thr Gln Phe Thr Gly Val Val Thr Glu Leu Phe Lys Arg Gly Asp
65                  70                  75                  80

Pro Ser Leu Gly Arg Ala Leu Ala Trp Met Ala Trp Cys Met His Ala
                85                  90                  95

Cys Arg Thr Leu Cys Cys Asn Gln Ser Thr Pro Tyr Tyr Val Val Asp
               100                 105                 110

Leu Ser Val Arg Gly Met Leu Glu Ala Met Lys His Asn Leu Leu Pro
               115                 120                 125

Trp Met Ile Ser His Gly Gly Gln Glu Glu Phe Leu Ala Phe Ser Leu
               130                 135                 140

His Ser Gln Ile Tyr Ser Val Ile Phe Asn Ile Lys Tyr Phe Leu Ser
145                 150                 155                 160

Lys Phe Cys Asn His His Phe Leu Arg Ser Cys Val Gln Leu Leu Arg
               165                 170                 175

Lys Cys Asn Leu Ile
               180
```

(2) INFORMATION FOR SEQ ID NO:19:

(i) SEQUENCE CHARACTERISTICS:
        (A) LENGTH: 280 amino acids
        (B) TYPE: amino acid
        (C) STRANDEDNESS: single
        (D) TOPOLOGY: linear (xi) SEQUENCE DESCRIPTION: SEQ ID NO:19:

```
Met Thr Arg Cys Thr Ala Asp Asn Ser Leu Thr Asn Pro Ala Tyr Arg
1               5                   10                  15

Arg Arg Thr Met Ala Thr Gly Glu Met Lys Glu Phe Leu Gly Ile Lys
            20                  25                  30

Gly Thr Glu Pro Thr Asp Phe Gly Ile Asn Ser Asp Ala Gln Asp Leu
        35                  40                  45

Pro Ser Pro Ser Arg Gln Ala Ser Thr Arg Arg Met Ser Ile Gly Glu
50                  55                  60

Ser Ile Asp Gly Lys Ile Asn Asp Trp Glu Glu Pro Arg Leu Asp Ile
65                  70                  75                  80

Glu Gly Phe Val Val Asp Tyr Phe Thr His Arg Ile Arg Gln Asn Gly
                85                  90                  95

Met Glu Trp Phe Gly Ala Pro Gly Leu Pro Cys Gly Val Gln Pro Glu
            100                 105                 110

His Glu Met Met Arg Val Met Gly Thr Ile Phe Glu Lys Lys His Ala
            115                 120                 125

Glu Asn Phe Glu Thr Phe Cys Glu Gln Leu Leu Ala Val Pro Arg Ile
            130                 135                 140

Ser Phe Ser Leu Tyr Gln Asp Val Val Arg Thr Val Gly Asn Ala Gln
145                 150                 155                 160

Thr Asp Gln Cys Pro Met Ser Tyr Gly Arg Leu Ile Gly Leu Ile Ser
                165                 170                 175

Phe Gly Gly Phe Val Ala Ala Lys Met Met Glu Ser Val Glu Leu Gln
                180                 185                 190

Gly Gln Val Arg Asn Leu Phe Val Tyr Thr Ser Leu Phe Ile Lys Thr
            195                 200                 205

Arg Ile Arg Asn Asn Trp Lys Glu His Asn Arg Ser Trp Asp Asp Phe
210                 215                 220

Met Thr Leu Gly Lys Gln Met Lys Glu Asp Tyr Glu Arg Ala Glu Ala
225                 230                 235                 240

Glu Lys Val Gly Arg Arg Lys Gln Asn Arg Arg Trp Ser Met Ile Gly
            245                 250                 255

Ala Gly Val Thr Ala Gly Ala Ile Gly Ile Val Gly Val Val Val Cys
            260                 265                 270

Gly Arg Met Met Phe Ser Leu Lys
            275                 280

(2) INFORMATION FOR SEQ ID NO:20:

(i) SEQUENCE CHARACTERISTICS:
        (A) LENGTH: 5408 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1665..1928

(xi) SEQUENCE DESCRIPTION: SEQ ID NO:20:

GAATTCTGGT AATTAGTTAA CAACCTTGA CAAGTTGTT TCACTTCTCT GAGTCTCAGT      60

TTCTCACTCA AAAATGGTGA ATAATTTGTA AGACTTCGCT AATAATCTAC GACTCTACAA    120

GAGGCAATAG GGTACTGTGG ACAGAGAGCA GGCTTTGGAA ACACACAAGA CTGGGTTTAG    180

ATTCCTGCAC TCCACCCAGT GTGTGACTTG GCCAAGCTTC TTCACTTCTC TAAACCCCCA    240

TCTGTGTATC TGTACAGGAA TGAATGAATG AGTATGTGCA GCCAAGCTAT GCAAACTCCA    300

GGTTAAAATA TTGCCTTGGG TTTTTTAGTA AATTGTTCAA GCCCATGACA TTCTAGCAGA    360
```

```
AAAAGCCTAG TGTCTCTTTC TTAAGGTGAT TGTGTCCATG TGTTTTCCAG GAACTCTATG      420

GGTTTCTCAA CCCAAATTCA CCCTGCCCTT GACCAAATGG CTCACCAGCT TCACGGATGC      480

TGCTCTGATG ACACACCCTG CAGTCAGCAT CTGCCCCTGC AGCTAGAATG GATTTCTGAG      540

TGGGCATTAG CTGGGGGATA CCACATGGGC ACCAATGTCA CAGATCTTCT GTCACAGTCC      600

ACCCCGAACC ATTGCTTCTC AAATCATAAT CCCTTAGCAG GACAGCTAGG TGCAGCACGC      660

ATGACACAAA CACCAGCCCT TGCCTACAAT CTCAGCCACT ATCTTGAGTC TGAGCAACTA      720

GTCTAGTGGC AGCCGCGCCC TTCCTTTTCA AGAGAGTTCT GGGATCAGAT CCTTTCACAA      780

ACAGATCCCT CCCCACCCTG CCTGTTGTCC AGGTCTGCAC ACTGAAAAGT AAGACAGCAT      840

TTGCTAAGCC ATATTTCAAA AGTTTGCTT ATACCTTCAT CTCAGGACAA CAAGTGCCTG       900

CTTAAGAGCC TTATGTTTGT GTAACTGGTA TTTTTTTTTC CCCTGACCTT CCAAGGCCTA      960

GTCTACTTTC TCCCTCCCTA GCTGAACAAA AGTGAAGTTG AAATAATTTG AACTACCCCT     1020

TTTAGTGGGC AGCCCATTTG ATTTTTACCT TAGCCAGAGC CTTAATTTGT CCATGTGAGC     1080

ATAGCAGTAC CTTGCAGCAC CTGAGGCACA ATACATTGTT TAAAGAGTGA CAGTGCGTCC     1140

CATTCCAATA GAACCACAC TCAGAGCAAA GGTTCCCTCT CCTGTGTGGA GAGTGACCCA      1200

TGGTAGAAAA TTTGCAGACT TCGTTACCTC TTCATCAGTT GAAAAATCTA TTTATTCATT     1260

TATGCATTTA ATTTTCCCTA TCTAAGCCAG GGATAGTCAA ACATTTTCTG TAAAGGGCCA     1320

AGTAGCATGA TAAATATGTT AGGCTCTGCA GGCCACTTAC AGTTTTGTCA TGTATTCTTT     1380

TTTTGCTCCC TGTTTGTATT ATTTTGTTTA CAATGCTTTA AAAATGTAAA AAAACAGATG     1440

ATCACTGGAG TCTCACGGGT CCCTCGGGCC ACACAGGGAC AAGCAAAGGC TACATCCAGA     1500

TACCAGAAAT GCACTGACGC CCGTTCCTGG AAGCTGGGCT CCCACTCAGC CCCTGGGAGC     1560

AGCAGCCTCC AGCCCCTTGG GACCTTCAAC TCCACCCTGC TGACCCACGC GGGTTGAGCC     1620

AGCATCCCTG GAGGCTGACA CTGTCCTCCA CTGAGACCTG AAAA ATG GCA TCG GGG     1676
                                                    Met Ala Ser Gly
                                                                 215

CAA GGC CCA GGG CCT CCC AGG CAG GAG TGC GGA AAG CCT GCC CTG CCC      1724
Gln Gly Pro Gly Pro Pro Arg Gln Glu Cys Gly Lys Pro Ala Leu Pro
            220                 225                 230

TCT GCT TCT GAG GAG CAG GTA GCC CAG GAC ATG GAG GGG TTT TCC GCA      1772
Ser Ala Ser Glu Glu Gln Val Ala Gln Asp Met Glu Gly Phe Ser Ala
        235                 240                 245

GCT ACG TTT TTT ACC ACC ATC AGC AGG AAC AGG AGG CTG AAG GGG CGG      1820
Ala Thr Phe Phe Thr Thr Ile Ser Arg Asn Arg Arg Leu Lys Gly Arg
    250                 255                 260

CCG CCC CTG CCG ACC CAG AGA TGG TCA CCT TGC CCC TCC AAC CTA GCA      1868
Pro Pro Leu Pro Thr Gln Arg Trp Ser Pro Cys Pro Ser Asn Leu Ala
265                 270                 275

GCA CCA TGG GGC AGG TGG GAC GGC AGC TCG CCA TCA CCA GGA CGA CAT      1916
Ala Pro Trp Gly Arg Trp Asp Gly Ser Ser Pro Ser Pro Gly Arg His
280                 285                 290                 295

CAA CCG GCA CTA TGACTTCGGA GTTCCAGACC ATGCTGCAGC ACCTGCAGCC          1968
Gln Pro Ala Leu

CACGGCAGAG AACGCCTACG AGTACTTCAC CAAGATCGCC TCCAGCCTGT TTGAGAGTGG    2028

CATCAACCGG GGCCGTGTGG TGGCTCTCCT GGGCTTCGGC TACCGTCTGG TCCTACATGT    2088

CTACCAGCAC GGCTTGACTG GCTTCCTGGG CCTGGTGACC CGCTTCGTGG TCTTCATGCT    2148

GCAACAAGGC ATCGCCCGGT GGATCTCGCA GAGGGGCGGC TGGGTGGCAG CCCTGGACTT    2208

GGGCAATAGT CCCATCCTGA ACGTGCTGGT GGTTGTGGGT GTGGTTCTGC TGGGCCAGTT    2268
```

```
TGTGGTAAGA AGATTCTTCA AATCATGACT CCCAGGGGTG TCCTTTGGGG TCCCAGCTGT    2328

GACCCCTGCC TGGACTTAAG CCAAGTCTTT GCCTTCCCCA CTCCCTTGCA GGGGTCACCC    2388

TTCAAAAGTA CAGAAGCTCT AGCAAGTGTG CACCCCCGCT GCGGAGGGCC CCTGCGTGGG    2448

GGCCAGTCAG GCTGCGGAGG CACCTCAACA TTGCACGGTG CTAGTGGGCC CTCTCTCTGG    2508

GCCCAGGGGC TGTGCCCTCC TCCCTTGGCT CTCTGGGACC TCCTTAGTCT TGTCTGCTAG    2568

GCGCTGCAGA GGCTGATAAC TTGGGGAAGC AAGAGACTGG GAGCCACTCC TCCCCAGTAA    2628

GTGTTTAACG GTTTTAGCTT TTTATAATAC CCTTGGGAGA GCCCATTCCC ACCATTCTAC    2688

CCAAGGCCGG GATGTCTGGG GTGTGGGGGT TGGTGGGTCG TAACCTACGT GCCCCAGGAT    2748

TCAGCTATTC TGGAAGATCA GAGCCTAAGA GCTAGGACTT GATCCTGGTC CTGGCCGTCC    2808

CTAAGCATCA TGTGTCCCAG GAGCAGGACT GACTGGGAGA GGGGACCAAG GTCCTACCCA    2868

GCTCTCCCCG TGCCCCCATT CCTCCTCCGG CCATACTGCC TTTGCAGTTG GACTCTCAGG    2928

GATTCTGGGC TTGGGGTGTG GGGCGGCGTG GAGTAACAGG CCAGAGCTGT CTGAACTTAT    2988

GTGTCAGAAG CCTCCAAGCC TGCCTCCCAA GGTCCTCTCA GCTCTCTCCC TTCCTCTCTC    3048

CTTATAGATA CTTGCTCCCA ACCCATTCAC TACAGGTGAA GGCCCTCACC CATCCCTGGG    3108

GGCCTTGGGT GAGTGATGCG CTAAGGCCCC TCCCCGCCCA GACTACAGGG CTTGGTTTAG    3168

GGCTTGGTTT GTTATTTCAG GGATAAGGAG TAGGGAGTTC ATCTGGAAGG TTCTAAGTGG    3228

GAGAAGGACT ATCAACACCA CAGGAATCCC AGAGGTGGGA TCCTCCCTCA TGGCTCTGGC    3288

ACAGTGTAAT CCAGGGGTGG AGATAGGGAA CTGTGAATAC CTGAACTCTG TCCCCCGACC    3348

CTCCATGCTC CTCACCTTTC TGGGTCTCTC CTCAGTGTGG GGGTGAGAGT ACCTTCTCTA    3408

TCGGGCACAG CCTAGGGTGT TGGGGGTGAA GGGGGAGAAG TTCTTGATTC AGCCAAATGC    3468

AGGGAGGGGA GGCAGAAGGA GCCCACAGGC CACTCCCTAT CCTCTGAGTG TTTGGAAATA    3528

AACTGTGCAA TCCCATCAAA AAAAAAAGG AGAAAAAAT GTAAAAAACA TTCTTAGCTG    3588

TAAGCTACTT ATAGGGGGAT AAAGACAGGA CTGTTAATGG ACACAAACAT ACAGTTAGAG    3648

AGAAGAAATA AGTTCTGTCC AGGCACGGTG GCTCACACCT CTAACTCCAG CACTTTGGGA    3708

GACCAAAGTG GGAAGATCAT TTGAGTCCAG GAGTTCGAGA CCAGCCTGGA CAACATAGCA    3768

AGATCTTATC TCTACAGAAA ATTTAAAAAA AAGAAAAAAA CTAGCCGCAC AGGTCTGCAG    3828

TCCTAGCTAC TCGGGAGGCT AAGGTGGGAG AATCCTTGAA CCCAGGGATT TAGTTTGAGG    3888

TTGCAGTGAG CTATGATTGC ACCACTGCAC TCCAGACTGG GTGACTGAGT GAGACCCTGT    3948

CTCAAATATA AGAAGGAAC AAGTTCTAGT TTTCAATAGC GCAATAGGGT GAGTGCAGTT    4008

AGCAACAACA TATTGTGTAT TTCAAAATAG CTACAAGAGA GGATATGAAG TGTTCCCCCA    4068

AACAAGGAAT GATAACGTTC GAGGTGACAG ATACCTTAAA TACCCTGATT TGATCATTAC    4128

ACATTCAATG TATGTATCAA AATATTACAT GTACCCCACA AATTTGTGTA AATATTATGT    4188

ATCCACTTTT TAAAGTTGGC AGAGCCCAAA AGCACTACTA TGGCTTCCAG TGGTCACTGT    4248

GAGCACTGCC AGCTCAGCAA ATGTATCACC CAAAATCTGG GCAATGTGGG AAATTGGCTT    4308

CATGGCAGCT ATGGCTTTGC CACTGATAGG AATGATTTCC AGAGATACTT AATCCTCAAT    4368

TCGGACTCT TTGCTTCAGG AGTTTGGCTG GCCAGGAACA TGAGTGACAG TGACCTCTTG    4428

GCACTTCAGC TGGGGGTGTA GCCAAGCAGA CAAATGGAAT CTTGTGCTGA ACCCAAACCT    4488

TCTAGAAACA GAGCCTGTGA GCATCACAAG ATATGCCCTG ATGGAAGCTG AAGTTTAATT    4548

CAGCTGAGCG CTTGCCCCTT TCCAACCTGG TTTCTTTTTG TTCCTTGAGT CCAGTCAGAA    4608

TGCCATTCCC TGGCCAGCAG CCAGCCTTTA GTGACTGTCT CTGTTCTGCA AAGCTCTGTA    4668
```

```
TATAGTTACT GAGTTTCTGC AGGGGGTGAT CTTTGCTCTT GTCCTAAGAA ATAACTACAG    4728

TGTTTTAAGA AATATTTGAG GCCGGGTGCA GTGGTTCACA CCTGTAATCC AGCACTTTGG    4788

GAGGCCAAGG CAGGTGGATC ATGAGGTCAA GAGTTTGAGA CCATCATGGC CAACATGGTG    4848

AAACCCCATC TCTACTAAAA ATACAAAAAT TAGCTGGGTG TGGTGGCGGG CACCTGTAGT    4908

CCCAGCTACT CGGGAGGCTG AGGCAGGAGA ATCGCTTGAG CCTGGGAGGC GGAGGTTGCA    4968

CTGAGCCGAT ATCACGCCAC TGCACTCCAG CCTGGCGACA GAGCGAGACT CCATCTCAAA    5028

AAAAAGAAAA AATAAATAGT TGAAATAAAG ACTGCACATA AAGACAAAAA AAAGTTTAT     5088

AAAGTTAAAA AATAAAATAA AAAACAGGCT CCAGGCTGGA TTGGGCCCAG AGGCTGTAGG    5148

ACACAGACCC CCAGCCAATG ACTTCATAAA TCCGGATGTT AATCAGCCTC ACCTGGGAAT    5208

TTGGGGAGGG GACTCATTTT AAAACAGTTT CCTGGATTCT AACCCAACCC AGAAAATCAG    5268

ACTCTTTGAG CTAAATTCTT AAGCTCCCTG GTGATGATGA TGGAACCAGT TTATGGCTGA    5328

CCCCAGAGTA CCGTCTGAAA GACGTGCCAC ATCCCTCTCT CTCCAGCCTC CCCTTCTCCT    5388

CCATTCCCCA GGGAGAATTC                                                 5408
```

(2) INFORMATION FOR SEQ ID NO:21:

(i) SEQUENCE CHARACTERISTICS:
        (A) LENGTH: 88 amino acids
        (B) TYPE: amino acid
        (D) TOPOLOGY: linear (ii) MOLECULE TYPE: protein (xi) SEQUENCE DESCRIPTION: SEQ ID NO:21:

```
Met Ala Ser Gly Gln Gly Pro Gly Pro Pro Arg Gln Glu Cys Gly Lys
 1               5                  10                  15

Pro Ala Leu Pro Ser Ala Ser Glu Glu Gln Val Ala Gln Asp Met Glu
            20                  25                  30

Gly Phe Ser Ala Ala Thr Phe Phe Thr Thr Ile Ser Arg Asn Arg Arg
        35                  40                  45

Leu Lys Gly Arg Pro Pro Leu Pro Thr Gln Arg Trp Ser Pro Cys Pro
 50                  55                  60

Ser Asn Leu Ala Ala Pro Trp Gly Arg Trp Asp Gly Ser Ser Pro Ser
 65                  70                  75                  80

Pro Gly Arg His Gln Pro Ala Leu
                85
```

(2) INFORMATION FOR SEQ ID NO:22:

(i) SEQUENCE CHARACTERISTICS:
        (A) LENGTH: 210 amino acids
        (B) TYPE: amino acid
        (C) STRANDEDNESS: single
        (D) TOPOLOGY: linear (xi) SEQUENCE DESCRIPTION: SEQ ID NO:22:

```
Met Ala Ser Gly Gln Gly Pro Gly Pro Pro Arg Gln Glu Cys Gly Glu
 1               5                  10                  15

Pro Ala Leu Pro Ser Ala Ser Glu Glu Gln Val Ala Gln Asp Thr Glu
            20                  25                  30

Glu Val Phe Arg Ser Tyr Val Phe Tyr Arg His Gln Gln Glu Gln Glu
        35                  40                  45

Ala Glu Gly Val Ala Ala Pro Ala Asp Pro Glu Met Val Thr Leu Pro
 50                  55                  60

Leu Gln Pro Ser Ser Thr Met Gly Gln Val Gly Arg Gln Leu Ala Ile
```

-continued

```
               65                  70                  75                  80
Ile Gly Asp Asp Ile Asn Arg Arg Tyr Asp Ser Glu Phe Gln Thr Met
                85                  90                  95

Leu Gln His Leu Gln Pro Thr Ala Glu Asn Ala Tyr Glu Tyr Phe Thr
            100                 105                 110

Lys Ile Ala Thr Ser Leu Phe Glu Ser Gly Asn Trp Gly Arg Val Val
            115                 120                 125

Ala Leu Leu Gly Phe Gly Tyr Arg Leu Ala Leu His Val Tyr Gln His
        130                 135                 140

Gly Leu Thr Gly Phe Leu Gly Gln Val Thr Arg Phe Val Val Asp Phe
145                 150                 155                 160

Met Leu His His Cys Ile Ala Arg Trp Ile Ala Gln Arg Gly Gly Trp
                165                 170                 175

Val Ala Ala Leu Asn Leu Gly Asn Gly Pro Ile Leu Asn Val Leu Val
            180                 185                 190

Val Leu Gly Val Val Leu Leu Gly Gln Phe Val Val Arg Arg Phe Phe
            195                 200                 205

Lys Ser
    210
```